United States Patent [19]
Mak et al.

[11] Patent Number: 5,907,079
[45] Date of Patent: May 25, 1999

[54] MSH2 DISRUPTED MICE DEVELOP LYMPHOMAS

[75] Inventors: Tak W. Mak; Armin Reitmair, both of Toronto, Canada

[73] Assignee: Amgen Canada Inc., Mississauga, Canada

[21] Appl. No.: 08/588,521

[22] Filed: Jan. 18, 1996

[51] Int. Cl.$^6$ ............................. C12N 5/00; C12N 15/00; A61K 49/00

[52] U.S. Cl. ...................... 800/2; 800/DIG. 1; 424/9.1; 435/354

[58] Field of Search ................................. 800/2, DIG. 1; 424/9, 9.1; 435/354

[56] References Cited

U.S. PATENT DOCUMENTS 4,736,866   4/1988   Leder et al. ................................ 800/1

OTHER PUBLICATIONS

Aaltonen et al., "Clues to the Pathogenesis of Familial Colorectal Cancer," *Science*, 260:812–816 (May 7, 1993).
Aaltonen et al., "Replication Errors in Benign and Malignant Tumors from Heredity Nonpolyposis Colorectal Cancer Patients," *Cancer Res.*, 54:1645–1648 (Apr. 1, 1994).
Adra et al., "Cloning and Expression of the Mouse pgk–1 Gene and the Nucleotide Sequence of Its Promoter," *Gene*, 60:65–74 (1987).
Alani et al., "Interaction Between Mismatch Repair and Genetic Recombination in *Saccharomyces cerevisiae*," *Genetics*, 137:19–39 (May, 1994).
Anisimov, V. N., "Age and Dose–dependent Carcinogenic Effects of N–nitrosomethylurea Administered Intraperitoneally in a Single Dose to Young and Adult Female Mice," *J. Cancer Res. Clin. Oncol.*, 119:657–664 (1993).
Baker et al., "Male Mice Defective in the DNA Mismatch Repair Gene PMS2 Exhibit Abnormal Chromosome Synapsis in Meiosis," *Cell*, 82:309–319 (Jul. 28, 1995).
Bhattacharyya et al., "Mutator Phenotypes in Human Colorectal Carcinoma Cell Lines," *Proc. Nat'l. Acad. Sci., USA*, 91:6319–6323 (Jul., 1994).
Bishop and Thomas, "The Genetics of Colorectal Cancer," *Cancer Surveys*, 9(4):585–604 (1990).
Bradley et al., "Embryo–Derived Stem Cells: A Tool For Elucidating The Developmental Genetics Of The Mouse," In: *Current Topics in Developmental Biology*, Chapter 25, vol. 20, Yamada Science Foundation and Academic Press Japan, Inc., pp. 357–371 (1986).
Bradley et al., "Formation of Germ–Line Chimaeras From Embryo–Derived Teratocarcinoma Cell Lines," *Nature*, 309:255–256 (May 17, 1984).
Bronner et al., "Mutation in the DNA Mismatch Repair Gene Homologue hMLH 1 is Associated with Heredity Non–Polyposis Colon Cancer," *Nature*, 368:258–261 (Mar. 17, 1994).
Burks et al., "Microsatellite Instability in Endometrial Carcinoma," *Oncogene*, 9:1163–1166 (1994).
Cannon–Albright et al., "Common Inheritance of Susceptibility To Colonic Adenomatous Polyps And Associated Colorectal Cancers," *N. Engl. J. Med.*, 319(9):533–537 (1988).
de Wind et al., "Inactivation of the Mouse Msh2 Gene Results in Mismatch Repair Deficiency, Methylation Tolerance, Hyperrecombination, and Predisposition to Cancer," *Cell*, 82:321–330 (Jul. 28, 1995).
Connelly et al., "The Role of Transgenic Animals in the Analysis of Various Biological Aspects of Normal and Pathologic States," *Experimental Cell Research*, 183:257–276 (Aug., 1989).
Doetschman et al., "Targetted Correction of a Mutant HPRT Gene in Mouse Embryonic Stem Cells," *Nature*, 330:576–578 (Dec. 10, 1987).
Feinstein and Low, "Hyper–Recombining Recipient Strains in Bacterial Conjugation," *Genetics*, 113:13–33 (May, 1986).
Fishel and Kolodner, "Identification of Mismatch Repair Genes and Their Role in the Development of Cancer," *Curr. Op. Genet. Devel.*, 5:382–395 (1995).
Fishel et al., "Binding of Mismatch Microsatellite DNA Sequences by the Human MSH2 Protein," *Science*, 266:1403–1405 (Nov. 25, 1994).
Fishel et al., "Gene Conversion in *Escherichia coli* Resolution of Heteroallelic Mismatched Nucleotides by Co–Repair," *J. Mol. Biol.*, 188:147–157 (1986).
Fishel et al., "Purified Human MSH2 Protein Binds to DNA Containing Mismatched Nucleotides," *Cancer Res.*, 54:5539–5542 (Nov. 1, 1994).
Fishel et al., "The Human Mutator Gene Homolog MSH2 and Its Association with Heredity Nonpolyposis Colon Cancer," *Cell*, 75:1027–1038 (Dec. 3, 1993).
Flam, F., "Cancer Treatment: Will History Repeat for Boron Capture Therapy?" *Science*, 265:468 (Jul. 22, 1994).
Fung–Leung et al., "CD8 Is Needed for Development of Cytotoxic T Cells but Not Helper T Cells," *Cell*, 65:443–449 (May 3, 1991).
Gonzalez–Zulueta et al., "Microsatellite Instability in Bladder Cancer," *Cancer Res.*, 53:5620–5623 (Dec. 1, 1993).
Hammer et al., "Production of Transgenic Rabbits, Sheep and Pigs by Microinjection," *Nature*, 315:680–683 (Jun., 1985).

(List continued on next page.)

*Primary Examiner*—Deborah Crouch
*Attorney, Agent, or Firm*—Marshall, O'Toole, Gerstein, Murray & Borun

[57] ABSTRACT

Non-human mammals comprising a disrupted MSH2 gene are disclosed. More particularly, animals having a disruption in one or both alleles of the MSH2 gene or a homolog of the MSH2 gene are disclosed. Animals homozygous for the disruption are viable past the embryonic stage of development but show an increased incidence of lymphoma, intestinal adenomas and carcinomas, and squamous cell tumors of the skin. Specifically disclosed are mice whose genome comprises a disrupted MSH2 gene such that the mice exhibits an increase in the incidence of spontaneous lymphoma over the incidence of spontaneous lymphoma in wild type mice.

15 Claims, 10 Drawing Sheets

OTHER PUBLICATIONS

Han et al., "Genetic Instability in Pancreatic Cancer and Poorly Differentiated Type of Gastric Cancer," *Cancer Res.*, 53:5087–5089 (Nov. 1, 1993).

Honchel et al., "Microsatellite Instability in Muir–Torre Syndrome," *Cancer Res.*, 54:1159–1163 (Mar. 1, 1994).

Ionov et al., "Ubiquitous Somatic Mutations in Simple Repeated Sequences Reveal a New Mechanism for Colonic Carcinogenesis," *Nature*, 363:558–561 (Jun. 10, 1993).

Jones et al., "Mismatch Repair and Recombination in *E. coli*," *Cell*, 50:621–626 (Aug. 14, 1987).

Kat et al., "An Alkylation–Tolerant, Mutator Human Cell Line is Deficient in Strand–Specific Mismatch Repair," *Proc. Nat'l. Acad. Sci., USA*, 90:6424–6428 (Jul., 1993).

Kee and Collins, "How Prevalent is Cancer Family Syndrome?" *Gut*, 32:509–512 (1991).

Kuehn et al., "A Potential Animal Model for Lesch–Nyhan Syndrome through Introduction of HPRT Mutations into Mice," *Nature*, 326:295–298 (Mar. 19, 1987).

Kunkel, T.A., "Slippery DNA and Diseases," *Nature*, 365:207–208 (Sep. 16, 1993).

Leach et al., "Mutations of a mutS Homolog in Heredity Nonpolyposis Colorectal Cancer," *Cell*, 75:1215–1225 (Dec. 17, 1993).

Levinson and Gutman, "High Frequencies of Short Frameshifts in Poly–CA/TG Tandem Repeats Borne By Bacteriophage M13 in *Escherichia coli* K–12," *Nucleic Acids Research*, 15(13):5323–5338 (1987).

Li and Modrich, "Restoration of Mismatch Repair to Nuclear Extracts of H6 Colorectal Tumor Cells By a Heterodimer of Human MutL Homologs," *Proc. Nat'l Acad. Sci., USA*, 92:1950–1954 (Mar., 1995).

Lindblom et al., "Genetic Mapping of a Second Locus Predisposing to Hereditary Non–Polyposis Colon Cancer," *Nature Genetics*, 5:279–282 (Nov., 1993).

Loeb, L.A., "Mutator Phenotype May Be Required for Multistage Carcinogenesis," *Cancer Res.*, 51:3075–3079 (Jun. 15, 1991).

Lynch et al., "Genetics, Natural History, Tumor Spectrum, and Pathology of Hereditary Nonpolyposis Colorectal Cancer:An Updated Review," *Gastroenterology*, 104:1535–1549 (1993).

McCormick et al., "Lifetime Dose–Response Relationships for Mammary Tumor Induction by a Single Administration of N–Methyl–N–nitrosourea," *Cancer Res.*, 41:1690–1694 (May, 1981).

Merlo et al., "Frequent Microsatellite Instability in Primary Small Cell Lung Cancer," *Cancer Res.*, 54:2098–2101 (Apr. 15, 1994).

Modrich, P., "Mechanisms and Biological Effects of Mismatch Repair," *Ann. Rev. Genet.*, 25:229–253 (1991).

Nicolaides et al., "Mutations of Two PMS Homologues in Heredity Nonpolyposis Colon Cancer," *Nature*, 371:75–80 (Sep. 1, 1994).

Nyström–Lahti et al., "Mismatch Repair Genes on Chromosome 2p and 3p Account for a Major Share of Hereditary Nonpolyposis Colorectal Cancer Families Evaluable by Linkage," *Am. J. Hum. Genet.*, 55:659–665 (1994).

Papadopoulos et al., "Mutation of a mutL Homolog in Hereditary Colon Cancer," *Science*, 263:1625–1629 (Mar. 18, 1994).

Parsons et al., "Hypermutability and Mismatch Repair Deficiency in RER+ Tumor Cells," *Cell*, 75:1227–1236 (1993).

Parsons et al., "Mismatch Repair Deficiency in Phenotypically Normal Human Cells," *Science*, 268:738–770 (May 5, 1995).

Peltomäki et al., "Genetic Mapping of a Locus Predisposing to Human Colorectal Cancer," *Science*, 260:810–812 (May 7, 1993).

Peltomäki et al., "Microsatellite Instability Is Associated with Tumors That Characterize the Hereditary Non–Polyposis Colorectal Carcinoma Syndrome," *Cancer Res.*, 53:5853–5855 (Dec. 15, 1993).

Peto et al., "Cancer and Aging in Mice and Men," *Br. J. Cancer*, 32:411–426 (1975).

Ponz de Leon et al., "Identification of Hereditary Nonpolyposis Colorectal Cancer in the General Population," *Cancer*, 71(11):3493–3501 (Jun. 1, 1993).

Porter et al., "N7–cyanoborane–2'–deoxyguanosine 5'–triphosphate is a Good Substrate for DNA Polymerase," *Biochemistry*, 34:11963–11969 (Sep. 19, 1995) (Abstract).

Radman, M., "Mismatch Repair and the Fidelity of Genetic Recombination," *Genome*, 31:68–73 (1989).

Rayssiguier et al., "The Barrier to Recombination Between *Escherichia coli* and *Salmonella typhimurium* is Disrupted in Mismatc–Repair Mutants," *Nature*, 343(6248):396–401 (Nov. 23, 1989).

Reitmair et al., "MSH2 Deficient Mice are Viable and Susceptible to Lymphoid Tumours," *Nature Genetics*, 11:64–70 (Sep., 1995).

Rhyu et al., "Microsatellite Instability Occurs Frequently in Human Gastric Carcinoma,"0 *Oncogene*, 9:29–32 (1994).

Risinger et al., "Genetic Instability of Microsatellites in Endometrial Carcinoma," *Cancer Res.*, 53:5100–5103 (Nov. 1, 1993).

Schoenberg et al., "Microsatellite Mutation ($CAG_{24 \to 18}$) in the Androgen Receptor Gene in Human Prostate Cancer," *Biochem. Biophys. Res. Commun.*, 198(1):74–80 (Jan. 14, 1994).

Selva et al., "Mismatch Correction Acts as a Barrier to Homeologous Recombination in *Saccharomyces cerevisiae*," *Genetics*, 139:1175–1188 (Mar., 1995).

Shibata et al., "Genomic Instability in Repeated Sequences Is An Early Somatic Event In Colorectal Tumorigenesis That Persists After Transformation," *Nature Genet.*, 6:273–281 (Mar., 1994).

Shridhar et al., "Genetic Instability of Microsatellite Sequences in Many Non–Small Cell Lung Carcinomas," *Cancer Res.*, 54:2084–2087 (Apr. 15, 1994).

Stenbäck et al., "Initiation and Promotion at Different Ages and Doses in 2200 Mice II. Decrease in Promotion By TPA With Ageing," *Br. J. Cancer*, 44:15–23 (1981).

Strand et al., "Destabilization of Tracts of Simple Repetitive DNA in Yeast by Mutations Affecting DNA Mismatch Repair," *Nature*, 365:274–276 (Sep. 16, 1993).

Thibodeau et al., "Microsatellite Instability in Cancer of the Proximal Colon," *Science*, 260:816–819 (May 7, 1993).

Thomas and Capecchi, "Site–Directed Mutagenesis by Gene Targeting in Mouse Embryo–Derived Stem Cells," *Cell*, 51:503–512 (Nov. 6, 1987).

Thompson et al., "Germ Line Transmission and Expression of a Corrected HPRT Gene Produced by Gene Targeting in Embryonic Stem Cells," *Cell*, 56:313–321 (Jan. 27, 1989).

Tybulewicz et al., Neonatal Lethality and Lymphopenia in Mice with a Homozygous Disruption of the c–abl Proto–Oncogene, *Cell*, 65:1153–1163 (Jun. 28, 1991).

Umar et al., "DNA Loop Repair by Human Cell Extracts," *Science*, 266:814–816 (Nov. 4, 1994).

Umar et al., "Defective Mismatch Repair in Extracts of Colorectal and Endometrial Cancer Cell Lines Exhibiting Microsatellite Instability," *J. Biol. Chem.,* 269(20):14367–14370 (1994).

Wada et al., "Genomic Instability of Microsatellite Repeats and Its Association With the Evolution of Chronic Myelogenous Leukemia," *Blood,* 83(12):3449–3456 (Jun. 15, 1994).

Wooster et al., "Instability of Short Tandem Repeats (Microsatellites) in Human Cancers," *Nature Genet.,* 6(2):152–156 (Feb., 1994).

Worth et al., "Mismatch Repair Proteins MutS and MutL Inhibit RecA–Catalyzed Strand Transfer Between Diverged DNAs," *Proc. Nat'l. Acad. Sci., USA,* 91:3238–3241 (Apr., 1994).

Yee et al., "Microsatellite Instability and Loss of Heterozygosity in Breast Cancer," *Cancer Res.,* 54:1641–1644 (Apr. 1, 1994).

Young et al., "Genomic Instability Occurs in Colorectal Carcinomas But Not in Adenomas," *Hum. Mutat.,* 2:351–354 (1993).

Leach et al Cell 75: 1215, 1993.

Fishel et al Cell 75: 1027, 1993.

Connelly et al Exp. Cell Res 183: 257,1989.

Tybulewicz et al Cell 65: 1153, 1991.

Radman et al Nature Genetics 11: 64, 1995.

de Wind et al Cell 82: 321, 1995.

FIGURE 1A

```
XbaI
CTAGAAATTA GAAGGCACTC AGGCAGTACT GCACCCCATT AGCATGGAGA CTCTGCTGAG    60
ACTCTGACCC TTGTTGCTGT CGCATGTTAT GTTTTATCCA GCCTTAGAAT CAGGGAGGTT   120
TGTGTGGTAG CTTTGGCTCT AATGCTGTGT CACAGTGGAG TCTTGAATGT GTGTTAAATG   180
     EcoRI
GGCACCAGGG ATCAACTCAA TCCTGCAAGC AAGCGTGCTG ATCCAACAAA ATGAAACTGC   240
AAATATTCTT GGAATCTGTT CTTGCTCATT GCTTATGGTG ATTTTTTTAA AGTGGTTTA    300
                                                          AccI
TAGTTTTCCC AGACACGGTT TCTCTGTATA CCCCTGACTC CTTTGGCTGT CCTGGAACTC   360
ACTCTGTAGA GCAGGCTGGC CTTGAACTCG GAGATCTGCC TGCCTCTGCC TCCTGAATGC   420
TGAGATGAAA TGTGTGCGTG CACCACCACA GCTCTCTTGT GATCTGAACA GGGTTGTCAT   480
     ApoI
GATTTCTCAA ATTTCCCAAC TTTTAGGGGA AAGTACGTTG TGCTAGTTAA TTGGGATTTC   540
ATAAGGAAAG ACCTTGCTCT CTGTTTTTGA AGCATGAAGG ATACAGTGAA ACATTTAACC   600
```

FIGURE 1B

```
CCATGTTGAG GTTCAAGGCT TTTCAGATTT TGTTATAGCA AACTTGCTAA CTTTTTAAAC    660
                                                CvIJI
GGCCTTGAGC TAAGTCTATT ATAAGGTGTA TCTTATGTTT TTACAGGCTA CGTAGAGCCA    720
ATGCAGACGC TCAACGATGT GCTGGCTCAC TTAGACGCCA TTGTTAGCTT CGCTCATGTG    780
TCAAACGCAG CACCCGTTCC TTATGTACGA CCAGTCATCT TGGAGAAAGG AAAAGGGGAG    840
                     SphI
AATTATATTG AAAGCCTCCA GGCATGCTTG TGTTGAAGTT CAAGGATGAA GTTGCATTTA    900
                                                          XcmI
TTCCAAATGA CGTGCACTTT GAAAAAGATA AACAGATGTT CCACATCATT ACTGGTAAAA    960
AACAATTTTT TTTCTCTCTT CCTAATGATG ATAGAATGGA AATGTGTTTT CAATTAATGA    1020
AGAAAGTCTC TCTTTCTGGC ATTAAAGAAT GTATTACTCT GGTTGGTCAT ACATTCAGAT    1080
CCTGACTAGA AGGAAGACTT TTTGGGGTGG CTAAAGTTTA GGAGATAATA TTGTTTCAGT    1140
ATATAACTCA CGCCCTGGCT CACCAGAGCC AGGACTTGGA AATGGGTAG GAATGGTCTT    1200
CTGGAAAAGC TGCAGCCTAG GCCAGCACGC CTCGTAAGAC ACTCATGTGT TCATACTCAT    1260
```

FIGURE 1C

| | | | | |
|---|---|---|---|---|
|TTGAAAGGAG|GCTGAGCTGT|CCTGAGATAG|TAACTAGAAC|CAGAGACTAG|AAAATAAGAG|1320|
|AGAATTACAT|TGTAGAAATT|ATGGTTCCAT|CCTGTTAGTT|CCCTAAGTGG|GTATTTAAAT|1380|
|TATTTAACCC|AACCCAGATA|AGTAAATTGT|ACATTTTCCA|AAAGAAATGT|CGTGTAGCAT|1440|
|GGAGTTTACG|TGATTTGAGG|AGTTTGCCCA|GACTGGTTAC|ATATAACTAG|CCCACTTATT|1500|
|AATGAATACT|ATTACTGAGT|AGTCAGTCGG|GCGTAATCGA|CATCATTAAA|TGAGTCTGTG|1560|
|AGCCAGGAAG|TGTGTGTGCG|TAGTGGCCCA|CAGTGATGCT|CCAGCTTAGC|TGTGCGGTTT|1620|
|ATGATCCTAC|TCTCTGGTTA|GAGGGATCTG|TGTGGGTTTG|TCTGACTGAA|TGGTAAGAAA|1680|
|GTTGCATTTG|GGGCTGGCGT|GACAGTGACT|GTCCATGCAT|GTTTTTGAT|GGCTTGTGGG|1740|
|TGGGTTTGCA|TATCATTGTG|ACTTAAATAA|TTGTAATTGC|AGTTTTGGAC|TACTAGTAGC|1800|
|TTAATTGTTA|GTAGTGAAAG|AAATCAGTGG|CCTGGCATAT|AATTCACTTA|TAGGTCCCAA|1860|
|TATGGGAGGT|AAATCAACAT|ACATTCGTCA|GACCGGGGTG|ATTGTACTCA|TGGCCCAAAT|1920|
|CGGGTGTTTT|GTGCCCTGTG|AGTCGGCAGA|AGTGTCCATT|GTGGATTGCA|TCCTTGCTCG|1980|
|AGTCGGGGCT|GGTGACAGTC|AACTGAAAGG|CGTCTCCACA|TTCATGGCTG|AAATGCTGGA|2040|

Figure 1D

```
GACTGCTTCC ATCCTCAGGT ATGTGTCCTA GTCCCTTGAA AGTGGAGACG TGTGGCCCCG   2100
TTTATTTGA AATGCATTTG CAGATTTGTC TATAATATGC CACAGGTATT CTTAGTTTAG   2160
TGAGTGTTTG CCTGTGAATT GTATGTACTT TATATTATCT TAAAAGGCTG ATTGGAAGCT   2220
GTGTGTGATG GCTGCTCGCC TTAATCTCAG CACTTGGGAG GCACAGGCAG GTGGATGTTT   2280
GTGAGTTTGA GGCCAGTCAA GTCTGTGTAA TGAGCTCAAG GATAGCTGGA CCGCAAAGAC   2340
AGACCCTATC TCAAAAAGCC AGAGAGAGAA ATATGAAAGG TTACCAAAAT CACTAATGTG   2400
AGTTTATGT ATTCTGTTGC CTTGTGTTTA ACAAATACTG TACTACAGGT ATCCACTACC   2460
TCTGCCTCTT TCGTCTTTCT GTCCCCTCTG CCATGATGAG CCCTGGACTG CATTTTTAT   2520
CATGTAATTA TGCGTTTCAG GTCAGCAACC AAAGACTCCT TAATAATCAT TGATGAGCTG   2580
GGAAGAGGAA CCTCTACCTA TGATGGATTT GGGTTAGCAT GGGCTATATC AGATTACATT   2640
GCAACGAAGA TTGGTGCCTT TTGCATGTTT GCCACCCATT TTCATGAACT TACTGCTTTG   2700
GCCAACCAAA TACCAACTGT TAATAATCTA CATGTCACAG CGCTCACTAC TGAGGAGACC   2760
CTAACTATGC TTTACCAAGT GAAAAAAGGT GGGCTTCTCC GCTCAGCCGTG GCCCTCAGGG   2820
```

FIGURE 1E

```
CCTGAAGTGC CATTAGTGCA TTCTTTATTC TCCGTTGGGA TTAATTGCTT TTAAGAACAT  2880
ATTTACCTCT GGCTTTCTAG TCTACAGATG AGCAATATAC ATTATCTGTA TCAAAATGAT  2940
AACGTGGGAG ACAGGTTGGT TTATTATAGC TATCTGACTA TAGGTTGGTT TTGTTTTAA   3000
CGTAAAGGAG GATTGCAATT TCTTAAAGGA TCTATCTTAT TTTTAATTAG TGTATTATGC  3060
                                    XbaI
CTTGTGTGAA GGTTGGTGCA CATGACACAG AGT                               3093
```

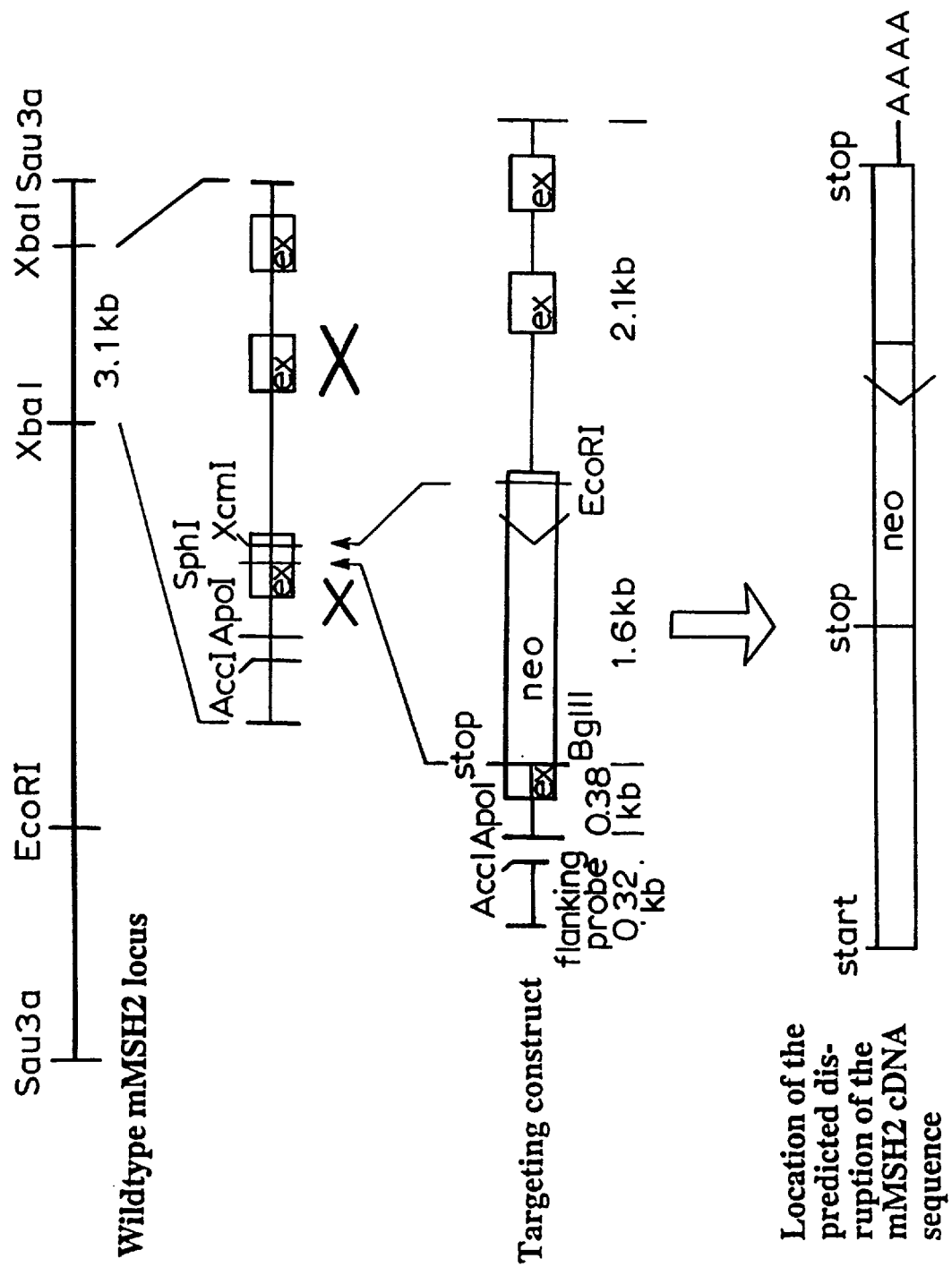

MSH2 DISRUPTED MICE DEVELOP LYMPHOMAS

BACKGROUND OF THE INVENTION

Hereditary Non-Polyposis Colon Cancer (HNPCC) is a common cancer predisposition syndrome characterized by a dominant mode of transmission and a high penetrance (Lynch et al., *Gastroenterology* 104:1535–1549 (1993)). Approximately 5% to 15% of colon cancers in industrialized nations have been attributed to HNPCC, suggesting an allele frequency that could be as high as 1 in 200 (Papadopoulos et al., *Science* 263:1625–1629 (1994); Ponz de Leon et al., *Cancer* 71:3493–3501 (1993); Kee and Collins, *Gut* 32:509–512 (1991); Cannon-Albright et al., *N. Engl. J. Med.* 319:533–537 (1988)). Although colon cancer is the principal cancer associated with HNPCC, more than 35% of the people in these families suffer other types of tumors of which endometrial and ovarian tumors are the most common. (Bishop and Thomas, Cancer Surveys 9:585–604 (1990)).

Genetic linkage studies have identified two HNPCC loci that are thought to account for nearly 90% of the affected families (Peltomaki et al., *Science* 260:810–812 (1993a); Lindblom et al., *Nature Genetics* 5:279–282 (1993); Nystrom-Lahti et al., *Am. J. Hum. Genet.* 55:659–665 (1994)). The first genetic locus characterized, which appears to account for approximately 50–60% of the HNPCC cases, was found to be located on chromosome 2p21 where mutations in the human MutS Homologue (hMSH2) gene were found to cosegregate with the disease (Fishel et al., *Cell* 75:1027–1038 (1993); Leach et al., *Cell* 75:1215–1225 (1993)).

The second locus, which appears to account for up to 20–30% of the HNPCC cases, was found to be located on chromosome 3p21 where mutations in the human MutL Homologue (hMLH1) gene were found to cosegregate with the disease (Bronner et al., *Nature* 368:258–261 (1994); Papadopoulos et al., *Science* 263:1625–1629 (1994)). These two genes code for homologues of the bacterial MutS and MutL proteins, which are essential components of the post-replication mismatch repair machinery (For a review see: Fishel and Kolodner, *Curr. Op. Genet. Devel.* 5:382–395 (1995)). Mutation of these genes in bacteria results in a generalized mutator (mut) phenotype that has been attributed to the absence of repair functions capable of recognizing mismatched nucleotides introduced into nascent DNA chains as a result of polymerase misincorporation errors. Such mismatches would subsequently lead to the passive accumulation of spontaneous mutations after a second round of DNA replication. Biochemical studies have shown that the MutS protein is involved in the initial mismatch recognition step and the MutL protein appears to link the excision repair machinery to mismatch recognition (Modrich, *Ann. Rev. Genet* 25:229–253 (1991)). These results support a direct role for mismatch repair functions in mutation avoidance.

Two other MutL homologues have been described, HPMS1 and hPMS2, that are related to the *S. cerevisiae* PMS1 gene which was originally identified as a contributor to "Post-Meiotic Segregants": a genetic phenomenon that suggested unrepaired mismatched nucleotides following chromosomal recombination (Nicolaides et al., *Nature* 371:75–80 (1994)). Mutations of these genes have been found in sporadic colorectal tumors and, in the case of hPMS2, in HNPCC families and may account for an additional 5–10% of HNPCC cases (Parsons et al., *Science* 268:738–470 (1995)).

The identification of hMSH2 and hMLH1 as genes in which mutations may predispose individuals to HNPCC, was facilitated by the observation that >85% of the tumors derived from these patients displayed instability of simple repetitive (microsatellite) sequences (Aaltonen et al., *Science* 260:812–816 (1993)). A similar nucleotide repeat instability was first observed in both *E. coli* and *S. cerevisiae* only when their respective mismatch repair genes were defective (Levinson and Gutman, *Nucleic Acids Research* 15:5313–5338 (1987); Strand et al., *Nature* 365:274–276 (1993)). Microsatellite instability has been observed in 5–85% of a variety of sporadic tumors (often termed: RER+ for replication error positive) suggesting that defects in mismatch repair or some related replication fidelity process may contribute widely to tumorigenesis (Ionov et al., *Nature* 363:558–561 (1993); Thibodeau et al., *Science* 260:816–819 (1993); Risinger et al., *Cancer Res.* 53:5100–5103 (1993); Young et al., *Hum. Mutat.* 2:351–354 (1993); Han et al., *Cancer Res.* 53:5087–5089 (1993); Peltomaki et al., *Cancer Res.* 53:5853–5855 (1993b); Gonzalez-Zulueta et al., *Cancer Res.* 53:5620–5623 (1993); Rhyu et al., *Oncogene* 9:29–32 (1994); Wada et al., *Blood* 83:3449–3456 (1994); Shridhar et al., *Cancer Res.* 54:2084–2087 (1994); Merlo et al., *Cancer Res.* 54:2098–2101 (1994); Wooster et al., *Nature Genet.* 6:152–156 (1994); Yee et al., *Cancer Res.* 54:1641–1644 (1994); Burks et al., *Oncogene* 9:1163–1166 (1994); Schoenberg et al., *Biochem. Biophys. Res. Commun.* 198:74–80 (1994); Honchel et al., *Cancer Res.* 54:1159–1563 (1994); Shibata et al., *Nature Genet.* 6:273–281 (1994); and Aaltonen et al., *Cancer Res.* 54:1645–1648 (1994)). In addition to microsatellite instability, cell lines that contain mutations in hMSH2 or hMLH1 are also defective for mismatch repair in vitro (Umar et al., *J. Biol. Chem.* 259:1–4 (1994a); Parsons et al., *Science* 75:1227–1236 (1993)), they display a generalized increase in spontaneous mutation frequency (Bhattacharyya et al., *Proc. Natl. Acad. Sci. USA* 91:6319–6323 (1994)) and are resistant to alkylating agents (Kat et al., *Proc. Natl. Acad. Sci. USA* 90:6424–6428 (1993)). The connection of microsatellite instability to a generalized mutator phenotype has suggested that the detection of such changes might be used as a convenient molecular diagnosis of a mismatch repair defect and a mutator phenotype in clinically presented tumors.

In both bacteria and yeast, MutS and its homologues play additional roles in genetic recombination. Mutational studies have shown that recombination between closely spaced markers is increased (Fishel et al., *J. Mol. Biol.* 188(2): 147–157 (1986); Feinstein and Low, *Genetics* 113:13–33 (1986); Jones et al., *Cell* 50:621–626 (1987)) and the length of DNA tracts exchanged between recombining chromosomes is reduced (Alani et al., *Genetics* 137:19–39 (1994)) in MutS (or MSH2) deficient cells. In addition, the tolerance of heterologous DNA sequence in recombining chromosomes is substantially increased in such bacterial or yeast cells (Rayssiguier et al., *Nature* 342(6248):396–401 (1989); Selva et al., *Genetics* 139:1175–1188 (1995)). These results suggest that mismatched nucleotides formed during genetic recombination provide a target for mismatch repair functions which, in the case of multiple mismatches, results in abortion of the recombination process (Radman, *Genome* 31(1):68–73 (1989); and Worth et al., *Proc. Nat. Acad. Sci. USA* 91:3238–3241 (1994)). This later observation has particular relevance to carcinogenesis since large scale rearrangements between non-homologous and/or partially homologous chromosomal sequences are a hallmark of tumor cells and may be indicative of widespread reduced-fidelity recombination processes.

Although the precise function of hMLH1 is poorly understood, hMSH2 has been purified and found to bind insertion/deletion loop-type (IDL) mismatched nucleotides with high affinity, and the single base pair G/T mismatch with lower affinity (Fishel et al., *Science* 266:1403–1405 (1994a); Fishel et al., *Cancer Res.* 54:5539–5542 (1994b)). IDL mismatched nucleotides have been proposed as an intermediate in microsatellite instability (Kunkel, *Nature* 365:207–208 (1993)). Furthermore, biochemical reconstitution studies that examine mismatch repair functions in vitro (Umar et al., *J. Biol. Chem.* 259:1–4 (1994a); Umar et al., *Science* 266:814–816 (1994b)), have resulted in the purification of two activities that appear to complement extracts derived from cell lines with known mutations in hMSH2 and hMLH1. Interestingly, both these purified complementing fractions consist of tightly complexed heterodimers. Protein extracts of the LoVo cell line, which contains deletions of both hMSH2 alleles, are complemented by a heterodimer that consists of hMSH2 (105 kDa) and a 160 kDa protein (P. Modrich, *Ann. Rev. Genet.* 25:229–253 (1991)), that has been cloned and identified as another MutS homologue a GT binding protein (GTBP/P160) and which has been found to co-purify as a heterodimer with hMSH2). There is some suggestion that the hMSH2/GTBP/160 heterodimer may bind mismatched nucleotides with a much higher affinity than either of the corresponding individual proteins. Protein extracts of the HCT116 cell line, which contains a deletion and a non-sense mutation of the hMLH1 alleles, are complemented by a heterodimer of hMLH1 (84 kDa) and hPMS2 (110 kDa) (Li and Modrich, *Proc. Nat. Acad. Sci. USA* 92:1950–1954 (1995)).

There are multiple possibilities by which faulty mismatch repair genes could result in the development of cancer (Fishel and Kolodner, *Curr. Op. Genet. Devel.* 5:382–395 (1995)). It has been hypothesized that cells with repair defects might have elevated rates of mutations (Loeb, *Cancer Res.* 51:3075–3079 (1991)). The accumulation of mutations could result in growth control defects—such as by interfering with check-point control mechanisms, tumor suppressors, or oncogenes that cause mutant cells to progress to malignancy. It is clear that an appropriate animal model is needed to investigate the possible role(s) of mismatch repair in tumorigenesis and to provide systems for testing of therapeutic interventions for the treatment of cancer and other diseases associated with mismatch repair deficiencies.

Although mutations in the human MSH2 gene co-segregate with malignant disease in a number of HNPCC kindreds, it has remained debatable whether mismatch repair is involved directly in the onset of tumorigenesis. Described below are mice having one or more disrupted MSH2 alleles. These mice are useful for the study of the role of mismatch repair in oncogenesis and as screening tools for suspected charcinogens and chemotherapeutic agents. While these mice are fertile and viable through at least 3 generations, they succumb to tumors at an early age with high frequency, supporting a role for MSH2 in tumorigenesis.

SUMMARY OF THE INVENTION

The present invention is directed to a non-human mammal, preferably a rodent having a disrupted MSH2 gene. The disruption may be introduced into the endogenous MSH2 gene by homologous recombination resulting in the insertion of a marker sequence into the gene, and preferably an exon of the gene. The marker sequence comprises, for example a gene encoding resistance to an antibiotic such as neomycin, although other selectable markers are also com- prehended by the invention. Preferably, the selectable marker is under the transcriptional control of a promoter capable of functioning in embryonic stem cells. One such promoter is the mouse phosphoglycerate kinase (PGK) promoter although other such promoters known to those of ordinary skill in the art may be used (e.g., the herpes simplex thymidine kinase gene promoter).

The invention is also directed to a non-human mammal having either one or both alleles of the MSH2 gene disrupted.

The invention is further directed to a mouse having a disrupted MSH2 gene wherein the disruption is introduced using a DNA construct comprising a mouse DNA corresponding to at least part of exon 11 of a human MSH2 gene and a neomycin resistance gene cassette comprising the mouse PGK promoter operatively linked to a neomycin resistance gene (PGK-neo), and wherein PGK-neo is inserted into the MSH2 gene in an antisense orientation via homologous recombination.

The invention is also directed to a mouse having a disrupted MSH2 gene wherein the disruption is introduced into the mouse by breeding an ancestor of the mouse with a donor mouse having a disrupted MSH2 gene as described above, and wherein the ancestor of the mouse has the same or a different genetic background than the mouse donating the disrupted MSH2 gene.

Another aspect of the present invention is a method for screening suspected carcinogens comprising the step of administering the suspected carcinogenic substance to a mouse having a disrupted MSH2 gene and monitoring the mouse for tumor associated morbidity and mortality. The carcinogens may be, but are not limited to chemical carcinogens, ionizing radiation, and electromagnetic fields. The carcinogens may also be capable of inducing free radical formation. Cells derived from the mice may also be utilized for screening potential carcinogenic agents.

The mammals of the present invention are also useful in the screening of antineoplastic agents, and more particularly they may be useful for screening chemotherapeutic agents for the treatment of lymphomas or other tumors resulting from defective mismatch repair in the subject animals. The method comprises administering the candidate antineoplastic agent to mouse having a disrupted MSH2 gene and a tumor, particularly a lymphoma, followed by monitoring the mouse for tumor associated morbidity and mortality, and wherein a successful chemotherapeutic agent decreases the morbidity and/or extends the life expectancy of the mouse. Cells derived from the mice of the present invention may also be used to screen for potential therapeutic agents which preferentially inhibit growth of mismatch repair deficient cells which may give rise to tumors.

In another of its aspects, the present invention is directed to an embryonic stem cell line having disrupted MSH2 gene. More particularly, a preferred embodiment of the invention comprises an embryonic stem cell line having the ATCC accession no. CRL11857.

BRIEF DESCRIPTION OF THE DRAWINGS

FIG. 1a–1e depicts the nucleotide sequence of an XbaI fragment of mouse genomic DNA containing 3 exons of the mouse MSH2 gene.

FIG. 2(a) is a map of the partial murine MSH2 locus (top), the targeting construct (middle) and the location of the neomycin mutation within the mouse MSH2 (mMSH2) cDNA sequence.

DETAILED DESCRIPTION

Figure 2B:
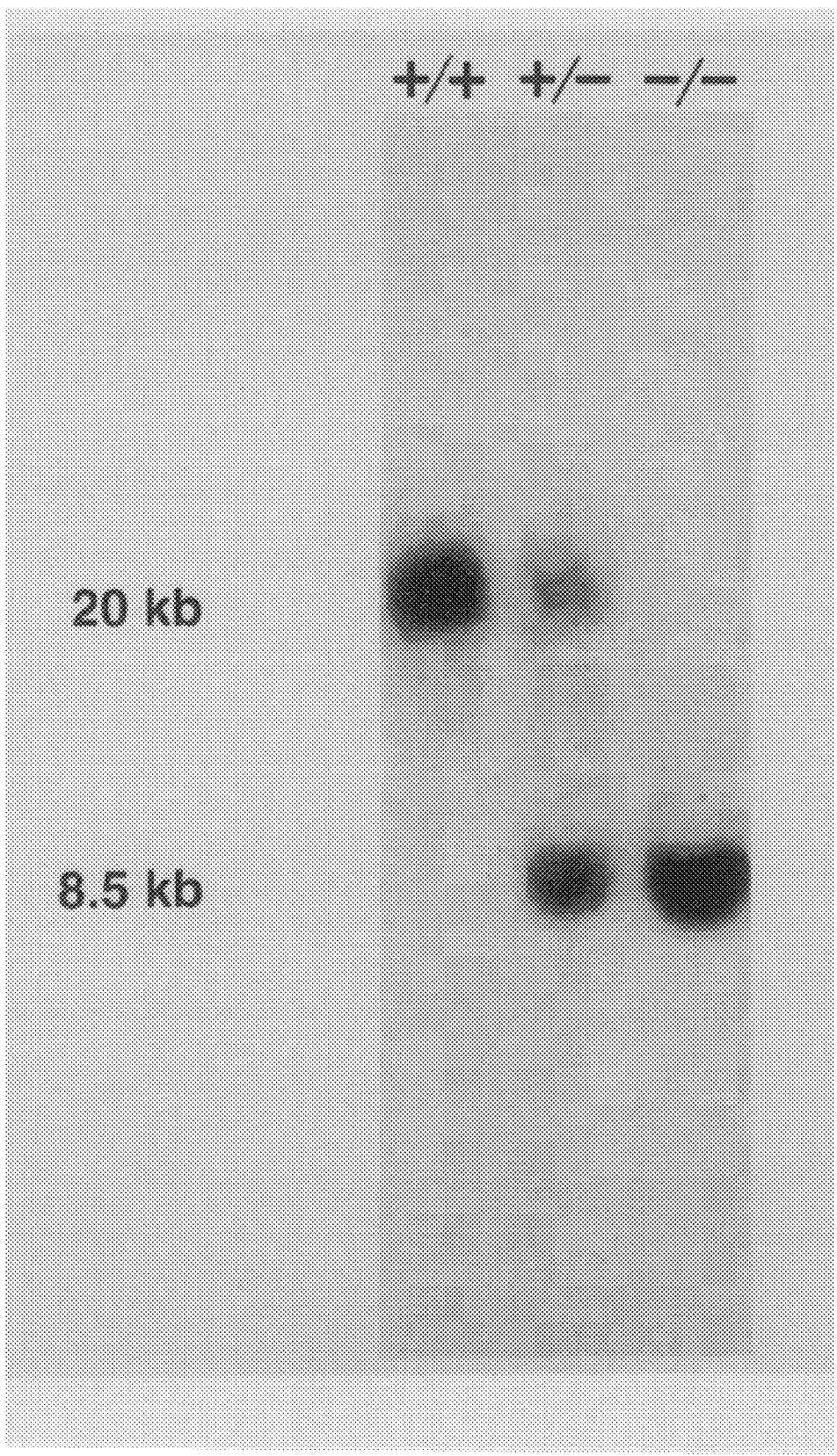
FIG. 2(b) depicts Southern blot analysis of DNA taken from offspring of heterozygous matings.

The mammals of the present invention comprise a disruption of an MSH2 gene of the mammal or the disruption of a homolog of the MSH2 gene (encoding mismatch repair proteins). The general strategy utilized to produce the mammals of the present invention involves the preparation of a targeting construct comprising DNA sequences homologous to the endogenous gene to be disrupted. The targeting construct is then introduced into embryonic stem cells (ES cells) whereby it integrates into and disrupts the endogenous MSH2 gene or homolog thereof. After selection of ES cells for the disruption, the selected cells are implanted into an embryo at the blastocyst stage.

The term "disruption" refers to partial or complete reduction of the expression of at least a portion of a polypeptide encoded by an endogenous target gene (such as the MSH2 gene) of a single cell, selected cells, or all of the cells of a mammal by introducing a targeting construct into the endogenous gene to be disrupted. The mammal may be heterozygous for the disruption, wherein one allele of the endogenous target gene has been disrupted. Alternatively, the mammal may be a homozygous for the disruption wherein both alleles of the endogenous gene have been disrupted.

The term "targeting construct" refers to a nucleotide sequence that is used to disrupt a target gene thereby decreasing or eliminating expression of a polypeptide encoded by the target gene in one or more cells of a mammal. The targeting construct typically comprises: (1) DNA from some portion of the endogenous target gene to be disrupted (one or more exon sequences, intron sequences, and/or promoter sequences); and (2) a marker sequence (typically a selectable marker such as a marker for antibiotic resistance) under the transcriptional control of the promoter capable of driving expression of the marker sequence in embryonic stem cells.

The targeting construct is introduced into a cell containing the endogenous target gene. The targeting construct can then recombine with one allele of the endogenous target gene (the MSH2 gene in the present case) and such recombination of the targeting construct can prevent or interrupt expression of the full-length endogenous MSH2 protein. Integration of the targeting construct into embryonic stem cell DNA is detected by selecting the cells for expression of the marker sequence. Introduction of the MSH2 targeting construct into the chromosomal DNA encoding MSH2 may occur via homologous recombination (i.e., via regions of the MSH2 targeting construct that are homologous or complementary to endogenous MSH2 DNA.

Typically, the targeting construct is introduced into an undifferentiated totipotent cell termed an embryonic stem cell (ES cell). ES cells are usually derived from an embryo or blastocyst of the same species as the developing embryo into which it can be introduced and is typically selected for its ability to integrate into and contribute to the germ line of a mammal when introduced into a mammal at the blastocyst stage of development. Thus, any ES cell line having this capability is suitable for use in the practice of the present invention. Preferred ES cell lines for generating mice of the present invention include the murine cell lines D3 (American Type Culture Collection, 12301 Parklawn Drive, Rockwell, Md. 20852–1776, U.S.A.) and E14 (see below). Accession No: CRL 1934.

The cells are cultured and prepared for introduction of the targeting construct using methods well known to the skilled artisan such as the methods set out by Robertson in "Teratocarcinomas and Embryonic Stem Cells, a Practical Approach, (Robertson, E. J. ed. IRL Press, Washington D.C. [1987]; Bradley et al., *Current Topics in Devel. Biol.* 20:357–371 (1986); by Hogan et al. in "Manipulating the Mouse Embryo": A Laboratory Manual, Cold Spring Harbor Laboratory Press, Cold Spring Harbor N.Y. 1986; and Fung-Leung et al. *Cell* 65:443–449). The targeting construct may be introduced into ES cells by any one of several methods known in the art including electroporation, calcium phosphate co-precipitation, retroviral infection, microinjection or other methods. ES cells expressing the marker sequence are then isolated and expanded.

The ES cells, modified as described above, are then introduced into a blastocyst at a suitable stage of development. Blastocysts are obtained by irritating the uterus of pregnant animals for example, by the methods described in Bradley and Robertson, supra. The suitable stage of development for the blastocyst is species dependent, however, for mice it is about 3.5 days post-fertilization.

While any blastocyst of the right age/stage of development is suitable for implantation of the modified ES cell, preferred blastocysts are male and have genes coding for a coat color or other phenotypic marker that is different from the coat color or other phenotypic marker encoded by the ES cell genes. In this way, the offspring can be screened easily for the presence of the knockout construct by looking for mosaic coat color (e.g. agouti) or the other phenotypic markers (indicating that the ES cell was incorporated into the developing embryo). Thus, for example, if the ES cell line carries the genes for white fur, the embryo selected will preferably carry genes for black or brown fur.

An alternate method of preparing an embryo containing ES cells that possess the targeting construct is to generate "aggregation chimeras". A morula of the proper developmental stage (about 2 ½ days post-fertilization for mice) is isolated. The zona pellucida can be removed by treating the morula with a solution of mild acid for about 30 seconds, thereby exposing the "clump" of cells that comprise the morula. Certain types of ES cells such as the RI cell line for mice can then be co-cultured with the morula cells, forming an aggregation chimera embryo of morula and ES cells, Joyner, A. L., "Gene Targetting", *The Practical Approach Series,* JRL Press Oxford University Press, New York, 1993.

A refinement of the aggregation chimera embryo method can be used to generate an embryo comprised of essentially only those ES cells containing the knockout construct. In this technique, a very early stage zygote (e.g., a two-cell stage zygote for mice) is given a mild electric shock. This shock serves to fuse the nuclei of the cells in the zygote thereby generating a single nucleus that has two-fold (or more) the DNA of a naturally occurring zygote of the same developmental stage. These zygotic cells are excluded from the developing embryo proper, and contribute only to forming accessory embryonic structures such as the extra-embryonic membrane. Therefore, when ES cells are co-cultured with the zygotic cells, the developing embryo is comprised exclusively of ES cells, see Joyner, A. L., supra.

After the ES cells have been incorporated into the aggregation chimera or into the blastocyst containing modified ES cells, they may be implanted into the uterus of a pseudopregnant foster mother. While any foster mother may be used, preferred foster mothers are typically selected for their ability to breed and reproduce well, and for their ability to care for their young. Such foster mothers are typically prepared by mating with vasectomized males of the same species. The pseudopregnant stage of the foster mother is important for successful implantation, and it is species dependent. For mice, this stage is about 2–3 days of pseudopregnancy.

Offspring (chimaeras) that are born to the foster mother may be screened initially for mosaic coat color or another phenotype marker where the phenotype selection strategy has been employed. In addition, or as an alternative, chromosomal DNA obtained from tail tissue of the offspring may be screened for the presence of the targeting construct using Southern blots and/or PCR which will not only detect the presence of the targeting construct but also the chromosomal location of the construct. The offspring that are positive for homologous recombination of the MSH2 targeting construct will typically be a mosaic of wild-type cells derived from the blastocyst and heterozygous cells, derived from injected ES cells.

Methods for producing transgenic mammals using microinjection including rabbits, pigs, and rats are described in Hammer et al., *Nature* 315:680–683 (1985).

If animals homozygous for the disruption are desired, they can be prepared by crossing heterozygous agoutis carrying the disruption in their germ line to each other; such crosses may generate animals homozygous for the disruption. Germ line transmission can be tested by crossing the chimera with a parental or other strain and the offspring screened for the presence of the targeting construct. Mammals homozygous for the disruption may be identified by Southern blotting of equivalent amounts of genomic DNA from mammals that are the product of this cross, as well as mammals of the same species that are known heterozygotes, and wild-type mammals. Probes to screen the Southern blots for the presence of the targeting construct in the genomic DNA can be designed as described below.

Other means of identifying and characterizing the offspring having a disrupted gene are also available. For example, Northern blots can be used to probe mRNA obtained from various tissues of the offspring for the presence or absence of transcripts as well as length differences encoding either the gene sought to be disrupted, the marker gene, or both. In addition, Western blots can be used to assess the level of expression of the disrupted gene by probing the Western blot with an antibody against the protein encoded by the disrupted gene. Protein for the Western blot may be isolated from tissues where this gene is normally expressed. Finally, in situ analysis (such as fixing the cells and labeling with antibody) and/or FACS (fluorescence activated cell sorting) analysis of various cells from the offspring can be conducted using suitable antibodies to look for the presence or absence of the gene product.

The terms "rodent" and "rodents" refer to all members of the phylogenetic order Rodentia including any and all progeny of all future generations derived therefrom.

The term "murine" refers to any and all members of the family Muridae, including without limitation, rats and mice.

The term "progeny" refers to any and all future generations derived or descending from a particular mammal, i.e., a mammal containing one or more knockout constructs introduced into its genomic DNA, whether the mammal is heterozygous or homozygous for the knockout construct. Progeny of any successive generation are included herein such that the progeny, the F1, F2, F3, generations and so on indefinitely containing the knockout construct are included in this definition.

The following examples describe the generation and characterization of MSH2-deficient mice and are presented by way of illustration and are not intended to limit the scope of the invention. Examples 1 describes the construction of the mouse MSH2 targeting vector. Example 2 describes the generation of embryonic stem cells having a disrupted MSH2 gene. Example 3 describes the generation of mice having disrupted MSH2 genes. Example 4 describes Western blot analysis of the MSH2 protein from mice. Example 5 describes the mutation rate in MSH2 deficient cells. Example 6 describes the development of lymphomas in $MSH2^{-/-}$ mice. Example 7 describes microsatellite instability in lymphomas. Example 8 describes lymphoid development in MSH2 deficient mice. Example 9 describes carcinogen testing using mice of the present invention. Example 10 describes the use of the mice of the present invention and cells derived therefrom in screening for chemotherapeutic agents.

Surprisingly, mice homozygous for the deficiency ($MSH2^{-/-}$) as described in the Examples below were viable. The MSH2 disruption was shown to segregate in a Mendelian fashion, and the animals were able to propagate for at least two generations. A significant fraction of $MSH2^{-/-}$ mice developed lymphoma at an early age. In addition, as the mice age, they develop a higher incidence of intestinal cancer, and squamous cell tumors than the wild-type or heterozygous mice. This is in contrast to their wild type and heterozygous siblings in which tumors were not detected.

The effects of differing genetic backgrounds on the phenotype arising from a defect in the MSH2 gene may be readily tested by introducing the MSH2 defect into mice of different genetic background by standard breeding techniques in which mice having defective MSH2 genes are bred to mice of differing genetic backgrounds. These mice can then be observed and analyzed for altered phenotypes resulting from the defective MSH2 gene.

EXAMPLE 1

Mouse MSH2 Targeting Vector

The human MSH2 DNA sequence and the description of its involvement in HNPCC was described by Fishel et al., *Cell* 75:1027–1038 (1993), and Leach et al., *Cell* 75:1215–1225 (1993). A human MSH2 (hMSH2) cDNA fragment was used as a hybridization probe to identify putative mouse MSH2 genomic DNA clones for use in deriving the mice of the present invention. The human fragment was generated by reverse transcription of total RNA of the human colon carcinoma cell line LIM1215 followed by PCR using primers specific for the hMSH2 gene.

Oligonucleotide primers were designed for PCR amplification of the evolutionarily most highly conserved region of the hMSH2 gene. The upstream primer was 5'-CACCTGTTCCATATGTACG (SEQ ID NO. 1) and the downstream primer was 5'-AAAATGGGTTGCAAA-CATGC (SEQ ID NO. 2) which correspond to amino acids 615–621 and 778–784 respectively. A 509 base pairs (bp) PCR amplification product was isolated and was cloned into pCRII (Invitrogen, San Diego, Calif.) via TA hybridization cloning (Sambrook et al., *Molecular Cloning, A Laboratory Manual,* Cold Spring Harbor Press, Cold Spring Harbor, N.Y. 1989).

The 509 bp PCR product was used as a hybridization probe to screen a mouse genomic library comprising a Sau3A partial digest of mouse 129/J (Jackson Laboratories, Bar Harbor, Me.) genomic DNA cloned into BamHI sites of Lambda Dash II (Stratagene, LaJolla, Calif.). Eight genomic clones were isolated based on their ability to hybridize to the 509 bp probe. Six of these clones were analyzed by digestion with different restriction enzymes (XbaI, SaIII, Not I, EcoRI, BamHI, HindIII), followed by Southern blotting and hybridization with the 509 bp probe. An approximately 3.1 kb genomic XbaI fragment derived from one of the six genomic clones was subcloned into pBluescript II KS(-) (Stratagene) and sequenced. The sequence of this 3.1 kb genomic XbaI fragment is set out in FIG. 1 (SEQ ID NO. 3). Three exons (FIG. 1) were identified by sequence comparison with the human cDNA (Fishel et al., supra and Leach et al., supra) using computer-software of the GCG-package (GCG, Madison, Wis.).

An ApoI-XbaI fragment was then isolated from the 3.1 kb XbaI subclone and was ligated into EcoRI and XbaI sites of pBluescript II KS(-). An adaptor DNA sequence containing four stop-codons (covering all three reading frames) and a BglII and an EcoRI site was inserted between the SphI and XcmI sites of the most upstream located exon of the mouse genomic DNA subclone (corresponding to exon 11 of the human gene) (see FIG. 2). The adaptor was generated by hybridization of 2 DNA oligonucleotides having the following sequence:

5'-CGTGATAGGTAACTGAGATCTCGGAATTCTGT-TCCACATCA-3' (SEQ ID NO. 3); and

5'-GATGTGGAACAGAATFCCGAGATCTCAGTTAC-CTATCACGCATG-3' (SEQ ID NO. 4).

The targeting construct, was constructed using a neomycin resistance gene cassette under control of the mouse phosphoglycerate kinase promoter derived from the pKJ-1 vector (Tybulewicz et al. Cell 65:1153–1163 (1991); and Adra et al., Gene 60:65–74 (1987)), both of which are incorporated herein by reference. PGK-neo was inserted in the antisense orientation into the BglII and EcoRI sites described above. These manipulations resulted in the deletion of 68 base pairs (corresponding to bases 1959–2026 of the mouse MSH2 cDNA available from GenBank under accession number X81143).

While 3 exons of the mouse MSH2 gene were cloned as described above, cloning of any other exon of the mouse gene may be accomplished using the techniques described above and using the available human sequence information (Fishel et al., Cell 75:1027–1038 (1993), and Leach et al., Cell 75:1215–1225 (1993)). This is possible because DNA sequence comparisons indicate that the DNA sequence of MSH2 genes are highly conserved between species. For example, mouse MSH2 cDNA encodes a protein having 92% amino acid homology with the protein encoded by human cDNA reflecting the highly conserved nature of the MSH2 gene. The choice of a site for the disruption of the MSH2 gene or any other gene is largely a matter of restriction site convenience in that disruption at any site is likely to ablate expression of the encoded protein rather than resulting in the production of a truncated protein.

EXAMPLE 2

Generation Of Embryonic Stem Cells Having A Disrupted MSH2 Gene

E14 embryonic stem cells derived from mouse strain 129/Ola (See, Kuehn et al., Nature 326:295–298 (1987); and Doetschman et al., Nature 330:576–578 (1987)) were maintained in the undifferentiated state by growth on a feeder layer of mitomycin C-treated embryonic fibroblasts in culture medium (Dulbecco's modified Eagle's medium) supplemented with leukemia inhibitory factor, e.g. 500–1000 units/ml), 15% fetal calf serum, L-glutamine and β-mercaptoethanol, (see Joyner, A. L., "Gene Targetting", The Practical Approach Series; JRL Press Oxford University Press, New York, 1993.).

The targeting construct described in Example 1 was linearized by digestion with HindIII prior to introduction into E14 cells by electroporation. E14 embryonic stem cells were transfected with 20 µg of linearized targeting construct DNA per 3×10$^6$ embryonic stem cells by electroporation using a Bio-Rad Gene Pulser, 0.34 kV, 0.25 mF (Hercules, Calif. and Melville, N.Y.). Approximately, 28 hours after transfection G418 selection (280 µg/ml) was started, and G418 resistant colonies were obtained after 10 days of selection. A polymerase chain reaction method was used to screen G418 resistant E14 cells for homologous recombination events according to a method described by Fung-Leung et al., Cell 65:443–449 (1991).

PCR screening of ES cell DNA for homologous recombination events utilized a primer specific for the neomycin resistance gene cassette 5'-GCCAGCTCATTCC-TCCACTC-3' (SEQ ID NO: 5) and an outside primer specific for the MSH2 gene 5'-CACCACCACAGCTCT-CTTGT-3' (SEQ ID NO: 6) located upstream of the construct. (See FIG. 2, pair of arrows.) Following an initial denaturation step (94° C. for 10 min), 40 cycles of PCR were performed using the following conditions: 94° C. for 1 min, 62° C. for 30 sec, 72° C. for 2 min. The purity of positive clones was subsequently examined by Southern blot analysis of EcoRI digested genomic DNA after hybridization with a probe flanking the targeting vector (See, FIG. 2) as well as a neomycin specific probe.

Of 1152 ES-clones tested, five contained the desired recombinational insertion mutation. The cell line used in the remainder of these studies was deposited under the terms of the Budapest Treaty with the American Type Culture Collection, 12301 Parklawn Drive, Rockville, Md. 20852 on Mar. 7, 1995 under accession number CRL11857.

EXAMPLE 3

Generation of Mice Having Disrupted MSH2 Gene

Chimeric mice were produced by injection of embryonic stem cells produced in Example 2 into 3.5-day-old blastocysts isolated from superovulated C57BL/6J females. The modified blastocysts were then implanted in pseudopregnant CD1 foster mice as described in Bradley et al., Nature 309:255–15 256 (1984); Bradley and Robertson, Curr. Top. Dev. Biol. 20:357–371 (1986); Thomas and Capecchi, Cell 51:503–512 (1987); Thompson et al., Cell 56:313–321 (1989); and Fung-Leung et al., Cell 65:443–449 (1991). Chimeras were mated with C57BL/6J (Jackson Laboratories, Bar Harbor, Me.) and the contribution of embryonic stem cells to the germline of chimeric mice was assessed by screening for the agouti coat color. Chimeric animals derived from all five ES clones tested succeeded in germline transmission of the mutation as demonstrated by Southern blot analysis of tail DNA.

Heterozygotes (MSH2$^{+/-}$) were intercrossed in a pathogen-free animal facility to generate MSH2$^{-/-}$ homozygous mice. Loss of both copies of the normal MSH2 allele was identified by Southern blot analysis (FIG. 2B).

The breeding of heterozygous mice resulted in viable wildtype, heterozygous and homozygous mutant F$_2$ progeny. In a comprehensive study, heterozygous breeding pairs were used to generate a total of 731 $F_2$ offspring out of which 716 animals were genotyped. The ratio of wildtype, heterozygous and homozygous mutant animals appears to follow a mendelian segregation of an expected 1:2:1 ratio (Table 1).

TABLE 1

Genotyping of $F_2$ Offspring

| Genotype | Number of Pups | Percentage |
|---|---|---|
| +/+ | 174 | 24.3% |
| +/− | 344 | 48.0% |
| −/− | 198 | 27.7% |
| TOTAL | 716 | 100% |

Furthermore, homozygous $MSH2^{-/-}$ mice are fertile and have been observed to produce offspring for at least three generations. These results demonstrate that MSH2-deficient mice can develop normally and that the mutation has no apparent effect on early animal viability.

EXAMPLE 4

Western Blot Analysis of MSH2 Mutant Mice

Mouse tail fibroblasts derived from wild type, heterozygous and homozygous mice were prepared by dounce homogenization with a loose pestle in PBS, 1 mM ethylenediamine-tetraacetic acid (EDTA), 0.5 mM phenylmethyl-sulfonyl fluoride (PMSF), 0.8 μg/ml Pepstatin and 0.8 μg/ml Leupeptin. Intact cells were isolated by centrifugation and dissolved in 10 mM EDTA, 1% sodium dodecylsulfate (SDS), 60% (v/v) glycerol, 0.5 % bromophenol blue and protease inhibitors and cellular debris removed by centrifugation. Approximately 20 μg of protein was separated by SDS polyacrylamide gel electrophoresis and transferred to nitrocellulose according to published methods (Maniatis et al., *Molecular Cloning*, Cold Spring Harbor, Cold Spring Harbor Laboratory (1982)). This Western blot was blocked overnight at 4° C. with 2% BSA and probed with a monoclonal antibody designated FEIL directed to the carboxyl terminus of the MSH2 protein (Oncogene Sciences, Cambridge, Mass.). The antibody probed blot was washed and developed by the alkaline phosphatase secondary antibody method according to the manufacturers' recommendations (Promega, Madison, Wis.). In separate experiments, a similar Western blot was probed with a monoclonal antibody designated GB12, directed to the amino terminus of the MSH2 protein, (Oncogene Science, Cambridge, Mass.) and with polyclonal rabbit antisera to isolated hMSH2 protein. No other MSH2 specific bonds were observed in this analysis.

Figure 3:
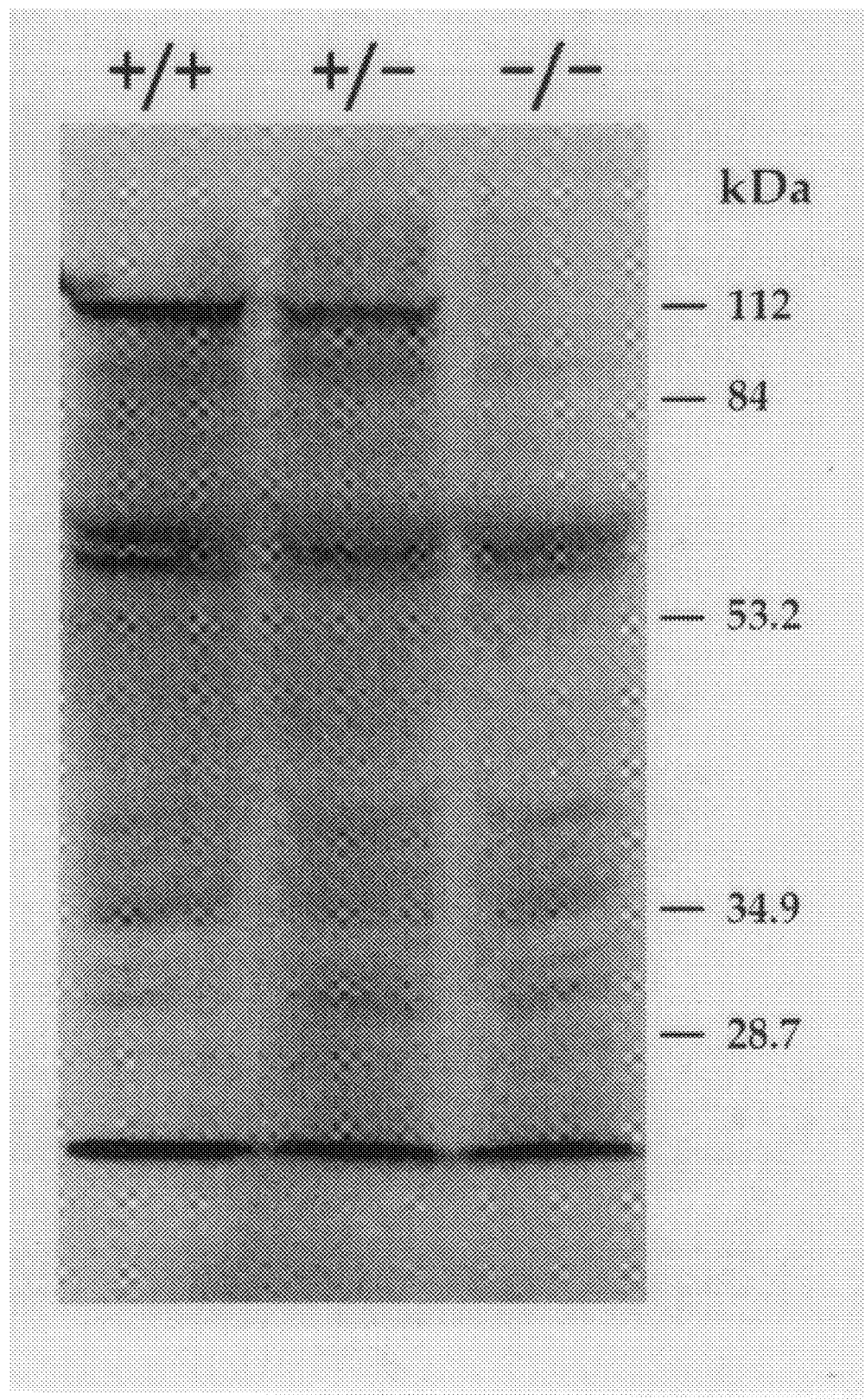
FIG. 3 depicts western blot analysis of MSH2 protein expression.

FIG. 3 shows the result of the analysis. Molecular weight markers are shown. Specific antibody recognition is observed with a 104 kDa protein that corresponds to the molecular weight of mouse MSH2. As illustrated in FIG. 3, the loss of both copies of the MSH2 gene resulted in the loss of detectable wildtype MSH2 protein expression. This data support the observation made in Example 1 that as a general rule, disruption of a gene using the methods described above, does not result in the production of a truncated protein but rather, results in a loss of detectable protein expression.

EXAMPLE 5

Mutation Rates in Genetically Defined Embryonic Fibroblasts

The effect of an MSH2 deficiency on mutation frequency at the hypoxanthine phosphoribosyl transferase (HPRT) locus as measured by resistance to 6-thioguanine (6-TG) was determined using primary embryonic fibroblasts derived from the genetically defined mice described above. Embryonic fibroblasts (see Joyner supra) were cultured in Dulbecco's modified Eagles medium (Gibco) supplemented with 10% fetal bovine serum (Hyclone, Logan, Utah). To measure the frequency of mutation at the HPRT locus as 6-thioguanine (6-TG) resistant clones, $5 \times 10^5$ cells were plated on a 100mm dish in the presence of 5 μg/ml of 6-TG. Plates were incubated for three weeks to allow colony formation before staining. Results of the assays are shown in Table 2.

TABLE 2

Mutation Frequency of the HPRT Locus

| Cell Line | Passage No. | Plating Efficiency (%) | Number of Cells Plated | Total Colonies | $TG^r$ Frequency |
|---|---|---|---|---|---|
| EF5 +/+ | 4 | 0.9 | $3.0 \times 10^6$ | 0 | $<3.3 \times 10^{-7}$ |
| EF6 +/+ | 4 | 1.7 | $3.0 \times 10^6$ | 0 | $<3.3 \times 10^{-7}$ |
| EF1 +/− | 4 | 2.1 | $3.0 \times 10^6$ | 0 | $<3.3 \times 10^{-7}$ |
| EF3 +/− | 4 | 0.6 | $3.0 \times 10^6$ | 0 | $<3.3 \times 10^{-7}$ |
| EF8 +/− | 4 | 0.5 | $3.0 \times 10^6$ | 0 | $<3.3 \times 10^{-7}$ |
| EF2 −/− | 4 | 0.8 | $3.0 \times 10^6$ | 62 | $1.88 \times 10^{-5}$ |
| EF4 −/− | 4 | 0.3 | $3.0 \times 10^6$ | 0 | $<3.3 \times 10^{-7}$ |
| EF7 −/− | 4 | 0.6 | $3.0 \times 10^6$ | 0 | $<3.3 \times 10^{-7}$ |

As shown in Table 2, no 6-TG resistant clones were detected in fibroblasts derived from embryos with wildtype or heterozygous MSH2 alleles. No 6-TG resistant clones were detected in fibroblasts derived from two individual MSH2 $^{-/-}$ embryos. However, a significant number of spontaneous 6-TG resistant clones arose from cells derived from a third embryo. It is possible that the number of 6-TG resistant clones in these samples is an underestimate as the plating efficiencies of the embryo fibroblasts were quite low (between 0.2% and 2%). It should be further noted that one rarely observes such "jackpot" 6-TG resistant clones in human tumor cell lines which contain wild type hMSH2 suggesting that the $MSH2^{-/-}$ embryonic fibroblasts possess a slightly elevated mutation rate that is partially obscured by the low plating efficiencies. At present, a consistent pattern of MNNG resistance has not been found for any of the embryo fibroblast cell lines tested with the caveat that plating efficiencies were also low in these experiments. Overall, these results suggest that embryo fibroblast cells from MSH2 deficient mice display a modest increase in spontaneous mutation frequency.

Sensitivity to N-methyl-N'-nitro-N-nitrosoguanidine (MNNG) was examined by exposing 100 or 1000 cells to 0, 5, 10, 20, or 30 μM of the drug for 90 min. No consistent pattern of sensitivity to MNNG was seen.

EXAMPLE 6

Development of Lymphomas in $MSH2^{-/-}$ Mice

Seven homozygous mutant mice between 2–5 months of age developed severe tumor-related illness and were sacrificed or were found dead. Mouse tissues were fixed in 10% buffered formalin and embedded in paraffin, or snap frozen in liquid nitrogen and stored at −70° C. For histological analysis sections were cut in 5 μm thick sections and stained with hematoxylin and eosin (H&E).

Six of these mice have been autopsied and found to have lymphoma (Table 3). The seventh mouse has presented with an enlarged thymus, the etiology of which has not yet been determined. In four of the mice analyzed, autopsy revealed striking enlargement of various organs (thymus max. 1.0 g; spleen max. 0.68 g; liver max.3.1 g), including lymph nodes. In the two mice without gross organ enlargement there was microscopic evidence of lymphoma infiltration.

This analysis revealed that the lymphoma of this mouse was in fact of B-cell origin, while two lymphoblastic lymphomas analyzed were of T-cell origin (see Table 3). None of the wild type or heterozygous littermates (~200) developed tumors within the same period of observation.

TABLE 3

Lymphoma Characterization in Homozygous Mutant Mice

| Mouse | Age (Months) | Lymphoma | Immunophenotype | Thymus | Spleen | Lymph Node | Bone Marrow | Liver |
|---|---|---|---|---|---|---|---|---|
| A1 | 4 | Lymphoblastic | | + | + | | | − |
| A15 | 3.5 | Lymphoblastic | B220−, CD4+, CD8+ | ++ | ++ | ++ | + | + |
| F8 | 4 | Lymphoblastic | B220−, CD4−, CD8+ | ++ | ++ | ++ | | ++ |
| J3 | 4 | Lymphoblastic | | ++ | ++ | ++ | + | ++ |
| S9 | 2.5 | Lymphoblastic | | ++ | + | − | | + |
| A5 | 4.5 | Immunoblastic | B220+, CD4−, CD8− | − | + | + | | + |

Histological evidence revealed that five mice had lymphoblastic lymphomas, which appeared as sheets of relatively monotonous cells with scattered tangible body macrophages giving a "starry sky" appearance. The thymus has also been replaced by lymphoma infiltrate. The lymphoma cells have scant cytoplasm enlarged round nuclei, irregular nuclear contours, stippled chromatin, inconspicuous nucleoli, and numerous mitotic figures. Histologic examination of internal organs in these mice revealed that the lymphoma was widely disseminated in most animals. In the liver, the lymphoma infiltrate was predominantly portal, with sinusoidal collections of cells also present in mice with more severe dissemination. Splenic distribution ranged from predominantly trabecular (white pulp) to massive parenchymal replacement. In kidney small infiltrations of lymphoma cells between renal tubules were seen. These infiltrates were scattered and focal within the renal cortex. In two mice scattered clusters of atypical cells were identified in bone marrow, however, definite involvement with lymphoma could not be established by microscopic examination. In one mouse in which a peripheral smear was examined, numerous abnormal circulating cells were identified, consistent with progression to leukemia, and coincident with massive bone marrow infiltration which was also identified in that mouse. In another mouse the histologic features of the lymphoma were more suggestive of an immunoblastic lymphoma; the nuclei had more prominent nucleoli, and there was a thin-to-moderate rim of amphophilic cytoplasm. In this mouse the thymus could not be grossly identified.

The cellular origin of the lymphomas was then investigated using several T-cell and B-cell specific markers as follows.

Frozen sections (7–10 μm) were air dried, fixed for 10 min. in 100% acetone at −20° C., air dried again for 30 min., and rehydrated in TBS (pH 7.4) 10% FCS. Sections were then blocked with TBS (pH 7.4) 10% hamster serum and stained with anti-CD4-Biotin, anti-CD8-Biotin, and B220-Biotin (all Pharmingen, San Diego, Calif.) for 60 min. Sections were washed three times with TBS (pH 7.4) 10% FCS, incubated with ExtrAvidin-Alkaline Phosphatase (Sigma, St. Louis, Miss.) for 30 min., then washed three times with TBS (pH 8.0) and developed with New Fuchsin (DAKO, Carpinteria, Calif.) containing 11 mM Levamisole (Sigma, St. Louis, Miss.). After another washing step the sections were counterstained with Mayer's Hamalum solution (Mark, Darmstadt, Germany).

EXAMPLE 7

Lymphomas Display Microsatellite Instability

Microsatellite instability has been used as a hallmark of mismatch repair defects to investigate the possibility of mismatch repair defects. Various tissues were harvested from MSH2+/+, MSH2+/−, MSH2−/− mice for microsatellite analysis. DNA was extracted from fresh frozen tissues using Trizol (Gibco, BRL-Life Technologies, Bethesda, Md.) according to the manufacturer's instructions. For paraffin embedded tissue biopsy specimens, 5 μm-thick sections were examined by hematoxylin and eosin staining and areas corresponding to normal and tumor histology were marked on the matched biopsy specimens. DNA was extracted as crude preparations from these specimens using a proteinase K lysis mix (10 mM Tris pH 8.0, 100 mM KCl, 2.5 mM $MgCl_2$, 0.45% Tween-20 and proteinase K). The sections were briefly homogenized in the lysis mix and digested for 1 hr at 65° C. followed by 10 min. at 95° C. DNA was stored at −20° C.

To determine microsatellite status, DNA was genotyped at 1–9 of the following loci by PCR: D1Mit4, D2Mit16, D3Mit11, D5Mit10, D6Mit8, D7Mit12, D8Mit4, D9Mit17, D10Mit2 (Dietrich et al., 1992). All primer pairs for PCR genotyping were obtained from Research Genetics (Huntsville, Ala.). Primer labeling and PCR amplification were carried out according to the protocol supplied by Research Genetics for Mouse MapPairs with the following modification. A single primer (10–15 pM) of each primer pair was end-labeled using T4 polynucleotide kinase and $^{32}$P-dATP according to Maniatis (1989). An aliquot (4 μl) of the PCR products was mixed with formaldehyde dye mix (2 μl), denatured at 85° C. for 2 min. and electrophoresed on 7% polyacrylamide gels under denaturing conditions for 2–3 hr. Gels were dried and exposed to X-ray films from 12–72 hrs. Results of this analysis indicate that to the approximation of whole tissue analysis, microsatellites in these mice appeared to be relatively stable.

Analysis of microsatellite sequences at D1Mit4 and D10Mit2 show that in several lyphomnas at least one microsatellite locus in each tumor was present in novel allelic forms as compared to parental tissues. Furthermore, organ samples that were histologically found to be infiltrated by the tumor also displayed microsatellite instabilities. None of the tumor-free tissues showed microsatellite instability. These results suggest that the clonal origin of tumors greatly contributes to the detection of microsatellite instability.

Insertion/deletion loop-type (IDL) mismatch binding activity (Fishel et al., *Science* 266:1403–1405 (1994a)) in MSH2$^{+/+}$, MSH2$^{+/-}$ and MSH2$^{-/-}$ embryonic fibroblasts, and a lymphoma from the A15 MSH$^{-/-}$ mouse was also analyzed. Only when both copies of the MSH2 allele were defective was IDL mismatch binding activity lost. Lost IDL activity was restored by the addition of purified hMSH2. Because microsatellite instability in healthy MSH2$^{-/-}$ mice was not observed where IDL mismatch binding activity was absent it is likely that: (1) the microsatellite instability detection methods used were not sensitive enough to observe allelic aberrations in somatic cells, or, (2) some other functional alteration that might distinguish somatic cells from lymphoma cells (i.e. mutator phenotype) is required to observe microsatellite instability.

In addition to developing lymphomas at an early age, these mice develop intestinal adenomas, carcinomas, and squamous cell tumors of the skin either spontaneously, or after exposure to mutagenic agents. Moreover, if the occurrence of lymphomas could be abrogated by breeding the MSH2$^{-/-}$ mutation into RAG1$^{-/-}$ mutant mice or other strains with lower susceptibility to lymphomas, other malignancies might be seen.

EXAMPLE 8

Lymphoid Development is Normal in MSH2 Deficient Mice

Figure 4A:
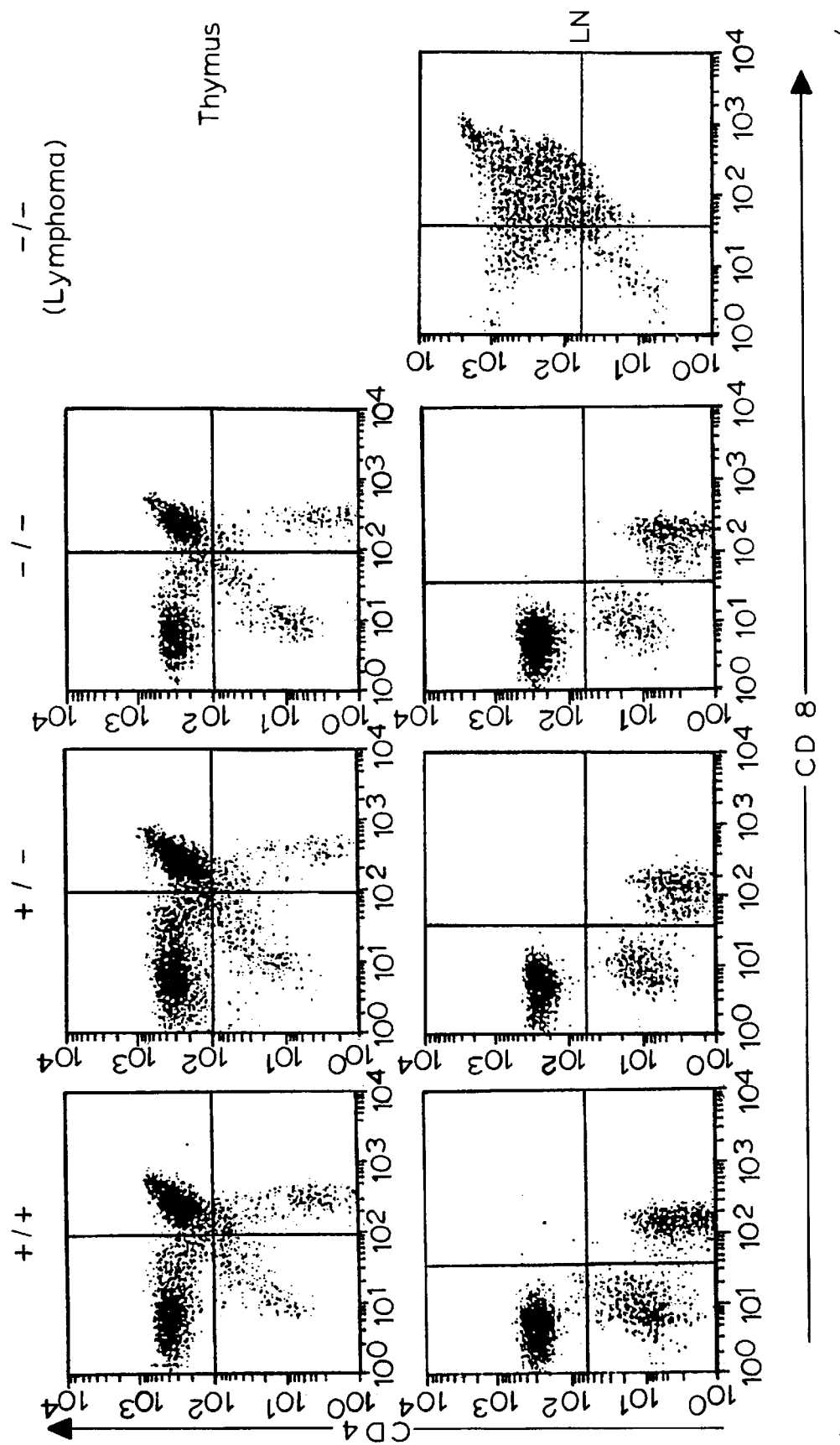
FIG. 4 illustrates the results of immunofluorescence analysis of T-cell specific surface antigens in MSH$^{+/+}$, MSH2$^{+/-}$, and MSH2$^{-/-}$ mice at six weeks of age.
Figure 4B:
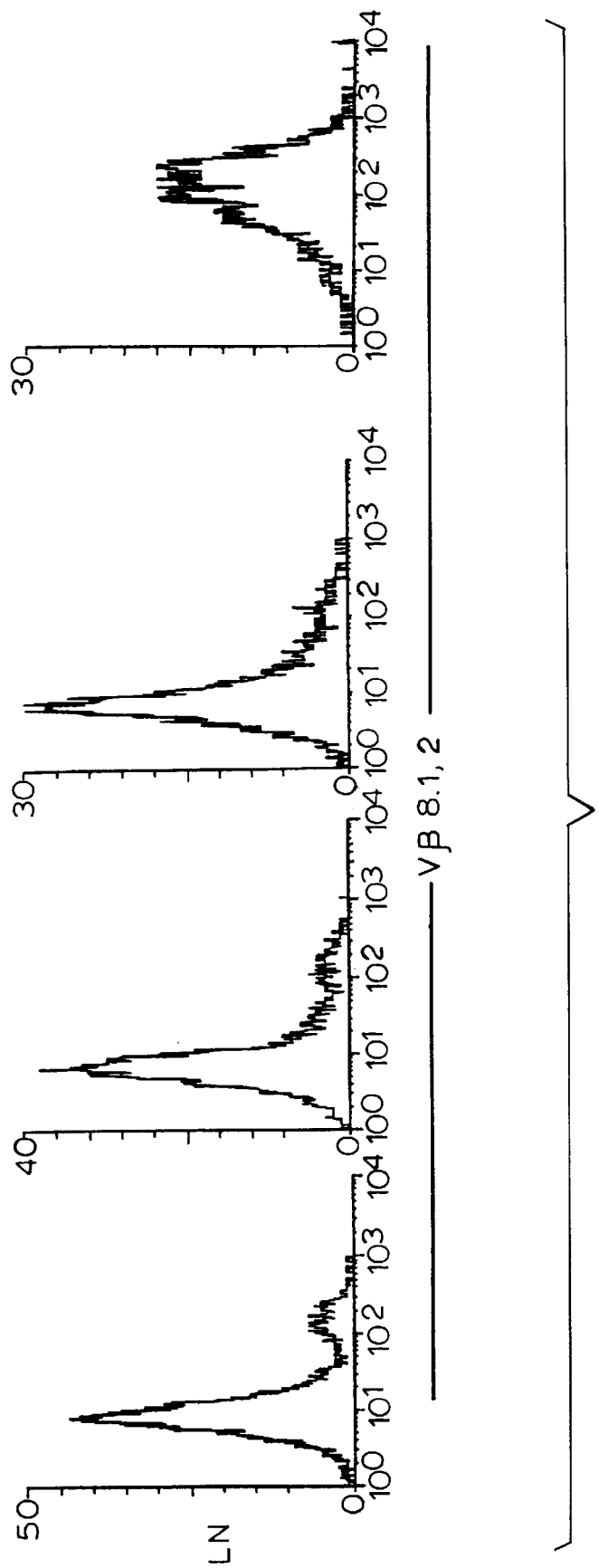

The increased occurrence of lymphoma in MSH2$^{-/-}$ mice prompted the examination of lymphocyte development in these mice. Healthy mice at six weeks of age were tested for the expression of several different cell surface molecules. Thymuses were isolated from healthy 6 week old mice and stained with anti-CD4 PE and anti-CD8 FITC described above. Lymphnodes (LN) from the same individuals and from one sick animal with lymphoma (A15) were stained with anti TCR Vβ 8.1, 8.2. In each instance 10000 viable cells were collected and analyzed on a FACScan (Becton-Dickinson). The results of the healthy animals compared to the sick mouse are from different experiments. Results of the study are shown in FIGS. 4A–4B.

Thymus, spleen and lymph node cells were stained with multiple monoclonal antibodies (MAbs). No difference between MSH2$^{+/+}$, MSH2$^{+/-}$ and MSH2$^{-/-}$ mice were seen in their expression of CD3, CD4, CD8, CD44, CD69, pan-CD45, B220, IgG and TCR Vβ 8.1, 8.2. A normal ratio of CD4/CD8 double positive, CD4/CD8 double negative as well as CD4 and CD8 single positive thymocytes were seen in all healthy MSH2$^{-/-}$ mice.

Using the above panel of surface markers, examination of other lymphatic organs also showed normal composition of T- and B-cells. A lymphoma sample from one mouse (A15; MSH2$^{-/-}$) was also examined. The majority of lymph node cells (68 %) were CD4/CD8 double positive and expressed mainly the T-cell receptor Vβ 8.1, 8.2 (86%). The staining for several other Vβ-elements of the T-cell receptor were in the normal range, or were reduced, which was due to an increase in Vβ 8.1, 8.2 positive T-cells. These results suggest that hematopoietic development is normal in MSH2$^{-/-}$ mice and that the lymphomas arise from otherwise normal progenitor hematopoietic cells to become tumors.

EXAMPLE 9

Carcinogen Testing in MSH2$^{-/-}$ and MSH2$^{+/-}$ Mice

Both MSH2$^{+/-}$ and MSH2$^{-/-}$ mice can be used to test materials and conditions suspected of contributing to or causing neoplastic disease. Also useful for testing such agents or conditions are animals produced by breeding MSH2 deficient mice into different genetic backgrounds. Because of the disruption of the MSH2 gene, the mice of the present invention represent a more sensitive model for screening suspected weak carcinogens.

The animals of the present invention are particularly useful as models for assessing age-related increases in tumor incidence because it is believed that age-related increase in tumor evidence results from accumulation of cell damage (mutation) induced by carcinogenic agents and/or the increase of the time of exposure to them (Petro et al., Br. J. Cancer 32:411–426 (1975); and Stenback et al., Br. J. Cancer 44:15–23 (1981). One of the main difficulties involved in the study of age-related incidence of tumors is that tumor latency may exceed the survival time of animals when exposed to a carcinogen is old age. This can easily lead to the erroneous conclusion that older animals are insensitive to carcinogens.

By virtue of their defects in mismatch repair, the animals of the present invention may accumulate DNA damage at a rate faster than wildtype mice thereby mimicking age-related accumulation of DNA damage. Using such animals makes it possible to detect carcinogens that would otherwise have been missed using older animals.

Methods for the screening of carcinogens are available and are well known to those of ordinary skill in the art. For example, Anisimov, *J. Cancer Res. Clin. Oncol.* 119:657–664 (1993) (incorporated herein by reference) describes a method for measuring the age and dose-dependant carcinogenic effects of N-nitrosomethylurea. Using the method described in Anisimov, mice of the present invention (homozygous or heterozygous) are injected intraperitoneally with the suspected carcinogen at a variety of doses. Other routes of administration may also be used. Animals are then observed for morbidity and/or mortality. Survival times for the animals may be measured as described in Anisimov. Histopathologic analysis is also carried out on animals to assess the presence of tumors and the nature of the tumor. Histopathologic analysis may be performed by examination of formalin-fixed, hematoxylin-eosin stained tissue sections from test animals or by other well-known methods including but not limited to immuno-histochemical staining. McCornick et al., *Cancer Res.* 41:1690–1694 (1981) (incorporation herein by reference) also teaches a method for carcinogen testing in animals which allows determination of cancer incidence resulting from administration of the carcinogen, the mortality rate, and the type of cancer induced.

The same types of studies may also be performed on mice of different genetic backgrounds (e.g. RAG-1) into which the disrupted MSH2 alleles have been introduced. This would provide the opportunity to determine the effect of mismatch repair defects on the development of tumors in mice with different susceptibility to tumors.

By way of illustration, studies were conducted in which wild-type, MSH2$^{-/-}$ and MSH2$^{+/-}$ animals were injected intraperitoneally with methylnitrosourea (MNU) at a dose of 50 mg/kg at seven weeks of age and were monitored for the development of lymphoma. The results showed 100% mortality in MNU treated MSH2$^{-/-}$ mice by 4 months of age, whereas wild-type mice all succumbed by 6.5 months of age. Untreated control MSH2$^{-/-}$ mice showed a 50% survival rate at 6.5 months of age. MSH2$^{+/-}$ mice injected with MNU also showed a survival rate of about 40% at 6.5 months of age. Wild-type mice and MSH2$^{+/-}$ control mice had a 100% survival rate at 6.5 months of age.

EXAMPLE 10

Testing of Chemotherapeutic Agents in MSH2 Deficient Mice

As discussed above, mice of the present invention have a higher spontaneous incidence of lymphoma than wild-type mice, and are thus useful for screening potential chemotherapeutic agents for treatment of lymphoma.

By way of example, the chemotherapeutic agent is administered to MSH2 deficient mice having lymphoma. Administration of the chemotherapeutic agent may be by any of several routes of administration including oral, parenteral, or other routes of administration depending on the particular agent being used. The proper dose of such agents will vary from agent to agent and is readily determined by one of ordinary skill in the art. The animals are then monitored for tumor associated morbidity and mortality. A successful chemotherapeutic agent is an agent that decreases tumor associated morbidity and/or extends the life span of the treated mouse.

Similarly, the mice may be used to screen for candidate prophylactic substances that decrease the incidence of tumors in MSH2 deficient mice. This screening is accomplished by administering the candidate prophylactic substance to a MSH2 deficient mouse ($MSH2^{+/-}$ or $MSH2^{-/-}$) and monitoring the animals for tumor formation. Dosages and routes of administration are readily determined by one of ordinary skill in the art.

Cells derived from these mice ($MSH2^{-/-}$, $MSH2^{+/-}$, and wild type) may be used in in vitro screening assays for potential chemotherapeutic agents. Cells from the animals are prepared according to methods well known in the art. Cells are then grown in the presence of various concentrations of the drug. Cell number is monitored on a periodic basis and growth curves are generated. Cell growth may be assessed by measuring increase in cell number or by harvesting the treated cells and determining their plating efficiency. A potentially useful chemotherapeutic agent may be identified by its ability to inhibit cell growth in $MSH2^{-/-}$ cells when compared to untreated $MSH2^{-/-}$ cells. Further, an effective chemotherapeutic agent would preferentially inhibit the growth of $MSH2^{+/-}$ cells while having markedly less effect on wild-type or $MSH2^{-/+}$ cells. This differential effect is known as the chemotherapeutic index. An appropriate chemotherapeutic index will differ for each drug and may be readily determined by one of ordinary skill in the art.

The foregoing examples are provided by way of illustration and are not intended to limit the scope of the claims as set out in the appended claims. All references referred to above are incorporated herein by reference.

---

We claim:

1. A mouse comprising a disrupted MSH2 gene, wherein said MSH2 gene is disrupted by a selectable marker sequence introduced into said mouse or an ancestor of said mouse at an embryonic stage, wherein said disruption prevents expression of MSH2, and wherein said mouse exhibits an increase in the incidence of spontaneous lymphoma over the incidence of spontaneous lymphoma in wild type mice.

2. The mouse of claim 1, wherein said disruption is introduced into said MSH2 gene by homologous recombination of said marker into an exon of said MSH2 gene.

3. The mouse of claim 2, wherein said disruption is the integration of a DNA fragment comprising exon 11 of a human MSH2 gene comprising a neomycin resistance gene inserted into said exon in an antisense orientation, and wherein said neomycin resistance gene is operatively linked to a promoter.

4. The mouse of claim 3, wherein said promoter is the mouse phosphoglycerate kinase promoter.

5. A mouse comprising a disrupted MSH2 gene, wherein the mouse is produced by breeding mice of claim 1, thereby producing offspring which comprise a disrupted MSH2 gene.

6. The mouse of claim 5, wherein said ancestor of said mouse is of a different genetic background than said mouse.

7. A method of screening suspected carcinogenic substances comprising the steps of:
   a) administering to the mouse of claim 1, one or more doses of said suspected carcinogen;
   b) monitoring said mouse for lymphoma associated morbidity and mortality; and
   c) determining carcinogenicity when said suspected carcinogen gives rise to lymphomas in said mice at a greater frequency as compared to the frequency in control mice.

8. The method of claim 7, wherein said suspected carcinogen is a chemical carcinogen.

9. The method of claim 7, wherein said suspected carcinogen is electromagnetic radiation.

10. The method of claim 7, wherein said suspected carcinogen is ionizing radiation.

11. The method of claims 8, 9, or 10 wherein said suspected carcinogen causes free radical formation.

12. A method for screening candidate antineoplastic agents comprising the steps of:
   a) administering said suspected antineoplastic agent to a mouse of claim 1;
   b) monitoring said mouse for lymphoma associated morbidity and mortality; and
   c) determining an antineoplastic agent when said candidate antineoplastic agent decreases lymphoma associated morbidity and mortality in said mouse as compared to control mice.

13. The method of claim 7 or 12, wherein the mouse is homozygous.

14. The method of claim 7 or 12, wherein the mouse is heterozygous.

15. An ES cell line having ATCC accession no. CRL11857.

* * * * *

UNITED STATES PATENT AND TRADEMARK OFFICE
CERTIFICATE OF CORRECTION

PATENT NO.    : 5,907,079
DATED         : May 25, 1999
INVENTOR(S)   : MAK et al.

It is certified that error appears in the above-identified patent and that said Letters Patent is hereby corrected as shown below:

Column 1, line 58, please delete "HPMSI" and insert in its place --hPMSI--.

Column 7, line 65, please delete "beterozygous" and insert in its place --heterozygous--.

Column 9, line 6, please delete SaIII" and insert in its place --SaII--

Column 9, line 29, please delete "GATGTGGAACAGAATFCCGAGATCTCAGTTAC" and insert in its place --GATGTGGAACAGAATTCCGAGATCTCAGTTAC--.

Column 13, line 64, please delete "11 mM" and insert in its place --1mM--.

Signed and Sealed this

Fifth Day of September, 2000

Attest:

Q. TODD DICKINSON

*Attesting Officer*    *Director of Patents and Trademarks*

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

CACCTGTTCC ATATGTACG                                   19

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

AAAATGGGTT GCAAACATGC                                  20

(2) INFORMATION FOR SEQ ID NO:3:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:3:

CGTGATAGGT AACTGAGATC TCGGAATTCT GTTCCACATC A                              41

(2) INFORMATION FOR SEQ ID NO:4:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GATGTGGAAC AGAATTCCGA GATCTCAGTT ACCTATCACG CATG                          44

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GCCAGCTCAT TCCTCCACTC                                                      20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CACCACCACA GCTCTCTTGT                                                      20

(2) INFORMATION FOR SEQ ID NO:7:

(i) SEQUENCE CHARACTERISTICS:
        (A) LENGTH: 3093 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:7:

CTAGAAATTA GAAGGCACTC AGGCAGTACT GCACCCCATT AGCATGGAGA CTCTGCTGAG     60

ACTCTGACCC TTGTTGCTGT CGCATGTTAT GTTTTATCCA GCCTTAGAAT CAGGGAGGTT    120

TGTGTGGTAG CTTTGGCTCT AATGCTGTGT CACAGTGGAG TCTTGAATGT GTGTTAAATG    180

GGCACCAGGG ATCAACTCAA TCCTGCAAGC AAGCGTGCTG ATCCAACAAA ATGAAACTGC    240

AAATATTCTT GGAATCTGTT CTTGCTCATT GCTTATGGTG ATTTTTTTAA AGTGGTTTTA    300

TAGTTTTCCC AGACACGGTT TCTCTGTATA CCCCTGACTC CTTTGGCTGT CCTGGAACTC    360

ACTCTGTAGA GCAGGCTGGC CTTGAACTCG GAGATCTGCC TGCCTCTGCC TCCTGAATGC    420

TGAGATGAAA TGTGTGCGTG CACCACCACA GCTCTCTTGT GATCTGAACA GGGTTGTCAT    480

GATTTCTCAA ATTTCCCAAC TTTTAGGGGA AAGTACGTTG TGCTAGTTAA TTGGGATTTC    540

-continued

```
ATAAGGAAAG ACCTTGCTCT CTGTTTTTGA AGCATGAAGG ATACAGTGAA ACATTTAACC    600
CCATGTTGAG GTTCAAGGCT TTTCAGATTT TGTTATAGCA AACTTGCTAA CTTTTTAAAC    660
GGCCTTGAGC TAAGTCTATT ATAAGGTGTA TCTTATGTTT TTACAGGCTA CGTAGAGCCA    720
ATGCAGACGC TCAACGATGT GCTGGCTCAC TTAGACGCCA TTGTTAGCTT CGCTCATGTG    780
TCAAACGCAG CACCCGTTCC TTATGTACGA CCAGTCATCT TGGAGAAAGG AAAAGGGGAG    840
AATTATATTG AAAGCCTCCA GGCATGCTTG TGTTGAAGTT CAAGGATGAA GTTGCATTTA    900
TTCCAAATGA CGTGCACTTT GAAAAAGATA AACAGATGTT CCACATCATT ACTGGTAAAA    960
AACAATTTTT TTTCTCTCTT CCTAATGATG ATAGAATGGA AATGTGTTTT CAATTAATGA   1020
AGAAAGTCTC TCTTTCTGGC ATTAAAGAAT GTATTACTCT GGTTGGTCAT ACATTCAGAT   1080
CCTGACTAGA AGGAAGACTT TTTGGGGTGG CTAAAGTTTA GGAGATAATA TTGTTTCAGT   1140
ATATAACTCA CGCCCTGGCT CACCAGAGCC AGGACTTGGA AAATGGGTAG GAATGGTCTT   1200
CTGGAAAAGC TGCAGCCTAG GCCAGCACGC CTCGTAAGAC ACTCATGTGT TCATACTCAT   1260
TTGAAAGGAG GCTGAGCTGT CCTGAGATAG TAACTAGAAC CAGAGACTAG AAAATAAGAG   1320
AGAATTACAT TGTAGAAATT ATGGTTCCAT CCTGTTAGTT CCCTAAGTGG GTATTTAAAT   1380
TATTTAACCC AACCCAGATA AGTAAATTGT ACATTTTCCA AAAGAAATGT CGTGTAGCAT   1440
GGAGTTTACG TGATTTGAGG AGTTTGCCCA GACTGGTTAC ATATAACTAG CCCACTTATT   1500
AATGAATACT ATTACTGAGT AGTCAGTCGG GCGTAATCGA CATCATTAAA TGAGTCTGTG   1560
AGCCAGGAAG TGTGTGTGCG TAGTGGCCCA CAGTGATGCT CCAGCTTAGC TGTGCGGTTT   1620
ATGATCCTAC TCTCTGGTTA GAGGGATCTG TGTGGGTTTG TCTGACTGAA TGGTAAGAAA   1680
GTTGCATTTG GGGCTGCGTG GACAGTGACT GTCCATGCAT GTTTTTTGAT GGCTTGTGGG   1740
TGGGTTTGCA TATCATTGTG ACTTAAATAA TTGTAATTGC AGTTTGGAC TACTAGTAGC    1800
TTAATTGTTA GTAGTGAAAG AAATCAGTGG CCTGGCATAT AATTCACTTA TAGGTCCCAA   1860
TATGGGAGGT AAATCAACAT ACATTCGTCA GACCGGGGTG ATTGTACTCA TGGCCCAAAT   1920
CGGGTGTTTT GTGCCCTGTG AGTCGGCAGA AGTGTCCATT GTGGATTGCA TCCTTGCTCG   1980
AGTCGGGGCT GGTGACAGTC AACTGAAAGG CGTCTCCACA TTCATGGCTG AAATGCTGGA   2040
GACTGCTTCC ATCCTCAGGT ATGTGTCCTA GTCCCTTGAA AGTGGAGACG TGTGGCCCCG   2100
TTTTATTTGA AATGCATTTG CAGATTTGTC TATAATATGC CACAGGTATT CTTAGTTTAG   2160
TGAGTGTTTG CCTGTGAATT GTATGTACTT TATATTATCT TAAAAGGCTG ATTGGAAGCT   2220
GTGTGTGATG GCTGCTCGCC TTAATCTCAG CACTTGGGAG GCACAGGCAG GTGGATGTTT   2280
GTGAGTTTGA GGCCAGTCAA GTCTGTGTAA TGAGCTCAAG GATAGCTGGA CCGCAAAGAC   2340
AGACCCTATC TCAAAAAGCC AGAGAGAGAA ATATGAAAGG TTACCAAAAT CACTAATGTG   2400
AGTTTTATGT ATTCTGTTGC CTTGTGTTTA ACAAATACTG TACTACAGGT ATCCACTACC   2460
TCTGCCTCTT TCGTCTTTCT GTCCCCTCTG CCATGATGAG CCCTGGACTG CATTTTTTAT   2520
CATGTAATTA TGCGTTTCAG GTCAGCAACC AAAGACTCCT TAATAATCAT TGATGAGCTG   2580
GGAAGAGGAA CCTCTACCTA TGATGGATTT GGGTTAGCAT GGGCTATATC AGATTACATT   2640
GCAACGAAGA TTGGTGCCTT TTGCATGTTT GCCACCCATT TTCATGAACT TACTGCTTTG   2700
GCCAACCAAA TACCAACTGT TAATAATCTA CATGTCACAG CGCTCACTAC TGAGGAGACC   2760
CTAACTATGC TTTACCAAGT GAAAAAAGGT GGGCTTCTCC GCTCAGCGTG GCCCTCAGGG   2820
CCTGAAGTGC CATTAGTGCA TTCTTTATTC TCCGTTGGGA TTAATTGCTT TTAAGAACAT   2880
ATTTACCTCT GGCTTTCTAG TCTACAGATG AGCAATATAC ATTATCTGTA TCAAAATGAT   2940
```

```
AACGTGGGAG ACAGGTTGGT TTATTATAGC TATCTGACTA TAGGTTGGTT TTGTTTTTAA    3000

CGTAAAGGAG GATTGCAATT TCTTAAAGGA TCTATCTTAT TTTTAATTAG TGTATTATGC    3060

CTTGTGTGAA GGTTGGTGCA CATGACACAG AGT                                 3093
```